United States Patent [19]

Sanner

[11] Patent Number: 5,714,487
[45] Date of Patent: Feb. 3, 1998

[54] 2,7-SUBSTITUTED OCTAHYDRO-PYRROLO [1,2-A]PYRAZINE DERIVATIVES

[75] Inventor: Mark A. Sanner, Old Saybrook, Conn.

[73] Assignee: Pfizer Inc., New York, N.Y.

[21] Appl. No.: 774,290

[22] Filed: Dec. 23, 1996

Related U.S. Application Data

[60] Provisional application No. 60/008,988, Dec. 21, 1995.

[51] Int. Cl.⁶ .................. C07D 487/04; A61K 31/495
[52] U.S. Cl. .................. 514/249; 544/322; 544/333; 544/349
[58] Field of Search .................. 544/322, 333, 544/349; 514/249

[56] References Cited

U.S. PATENT DOCUMENTS

| | | | |
|---|---|---|---|
| 4,400,511 | 8/1983 | Freed | 544/349 |
| 5,122,515 | 6/1992 | Bright et al. | 514/249 |

FOREIGN PATENT DOCUMENTS

| | | |
|---|---|---|
| 5097819 | 4/1993 | Japan. |
| 9410145 | 5/1994 | WIPO. |
| 9410162 | 5/1994 | WIPO. |
| 9604250 | 2/1996 | WIPO. |

OTHER PUBLICATIONS

U.S. application No. 08/750,479, Fliri et. al., filed Dec. 10, 1996.
Van Tol et al., *Nature* (London), 1991, vol. 350, p. 610.
Sunahara et al., *Nature* (London), 1991, vol. 350, p. 614.
Zawilska, *Neuroscience Lett.*, 1994, vol. 166, p. 203.
Diafi et al., *J. Het. Chem.*, 1990, vol. 27, p. 2181.

*Primary Examiner*—Mukund J. Shah
*Assistant Examiner*—Tamthom T. Ngo
*Attorney, Agent, or Firm*—Peter C. Richardson; Paul H. Ginsburg; Karen DeBenedictis

[57] ABSTRACT

This invention relates to compounds of formula I

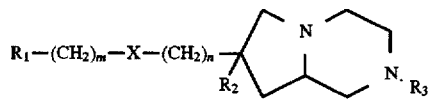

wherein $R_1$, $R_2$, $R_3$, X, m and n are defined as in the specification, their pharmaceutically acceptable salts and pharmaceutical compositions containing such compounds or their salts.

58 Claims, No Drawings

2,7-SUBSTITUTED OCTAHYDRO-PYRROLO [1,2-A]PYRAZINE DERIVATIVES

This application is based on United States provisional priority application Ser. No. 60/008,988, filed on Dec. 21st, 1995.

The present invention relates to novel pharmacologically active 2,7-substituted octahydro-1H-pyrrolo[1,2-a]pyrazine derivatives, their acid addition salts, and certain precursors thereto. The compounds of this invention are ligands for dopamine receptor subtypes, especially the dopamine $D_4$ receptor, and are therefore useful in the treatment of disorders of the dopamine system.

BACKGROUND OF THE INVENTION

Molecular biological techniques have revealed the existence of several subtypes of the dopamine receptor. The dopamine $D_1$ receptor subtype has been shown to occur in the least two discrete forms. Two forms of the $D_2$ receptor subtype, and at least one form of the $D_3$ receptor subtype, have also been discovered. More recently, the $D_4$ (Van Tol et al., *Nature* (London), 1991, 350, 610) and $D_5$ (Sunahara et al., *Nature* (London), 1991, 350, 614) receptor subtypes have been described.

The compounds of the present invention, being ligands for dopamine receptor subtypes, especially the dopamine $D_4$ receptor, are accordingly of use in the treatment or prevention of disorders of the dopamine system.

Dopamine D4 receptors are more prevalent in the brains of schizophrenic patients (Seeman, et al. *Nature*, 1993, 365, 441) relative to normal controls. Dopamine receptor antagonists are useful for the treatment of psychotic disorders, such as schizophrenia, and the compounds of the present invention, being ligands for dopamine receptor subtypes, especially the dopamine $D_4$ receptor, are accordingly of use in the treatment or prevention of psychotic disorders, especially affective psychosis, schizophrenia, and schizoaffective disorders.

Since dopamine receptors control a great number of pharmacological events and, on the other hand, not all these events are presently known, there is a possibility that compounds that act on the dopamine $D_4$ receptor may exert a wide range of therapeutic effects in animals.

WO 94/10162 (published May 11, 1994) and WO 94/10145 (published May 11, 1994) report that dopamine ligands are of use in the treatment and/or prevention of disorders of the dopamine system, including schizophrenia, nausea, Parkinson's disease, tardive dyskinesias and extrapyramidal side-effects associated with treatment by conventional neuroleptic agents, neuroleptic malignant syndrome, and disorders of hypothalamic-pituitary function such as hyperprolactinaemia and amenorrhoea.

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localization of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

The presence of D4 receptor mRNA in mouse retina has been noted (Cohen, et al. *Proc. Nat. Acad. Sci.*, 1992, 89, 12093), suggesting that dopamine and D4 receptors play a role in ocular function. The compounds of this invention may therefore be useful in the treatment of ocular disorders. Furthermore, D4 receptors influence melatonin biosynthesis in chick retina (Zawilska, Nowak, *Neuroscience Lett.*, 1994, 166, 203), and since melatonin has been used for the treatment of sleep disorders, the compounds of this invention may be useful for the treatment of sleep disorders as well.

Diafi, et al. (*J. Het. Chem.*, 1990, 27, 2181) describe certain 2,7-substituted pyrrolo[1,2-a]pyrazine derivatives of compound II for which no biological activity is claimed.

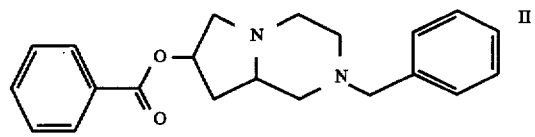

Nakamura, et al. (Jpn. Pat. Appl. JP05097819 A2 930420, published Apr. 20, 1993) describe derivatives and analogs of compound III which are antagonists of platelet activating factor (PAF) for the treatment of asthma and cardiovascular diseases.

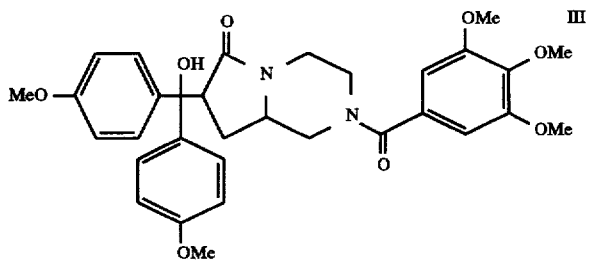

SUMMARY OF THE INVENTION

This invention relates to a compound of formula I

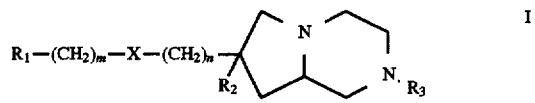

wherein $R_1$ is phenyl, naphthyl, benzoxazolonyl, indolyl, indolonyl, benzimidazolyl, quinolyl, furyl, benzofuryl, thienyl, benzothienyl, oxazolyl, benzoxazolyl;

$R_2$ is H or $(C_1-C_6)$alkyl;

$R_3$ is phenyl, pyridinyl, pyrimidinyl, pyrazinyl, or pyriydazinyl;

$R_4$ is H or $(C_1-C_6)$alkyl;

$R_5$ is H or $(C_1-C_6)$alkyl;

wherein each group of $R_1$ and $R_3$ may be independently and optionally substituted with one to four substituents independently selected from the groups consisting of fluoro, chloro, bromo, iodo, cyano, nitro, thiocyano, —$SR_4$, —$SOR_4$, —$SO_2R_4$, —$NHSO_2R_4$, —($C_1$–$C_6$) alkoxy, —$NR_4R_5$, —$NR_4COR_5$, —$CONR_4R_5$, phenyl, —$COR_4$, —$COOR_4$, —($C_1$–$C_6$)alkyl, —($C_1$–$C_6$)alkyl substituted with one to six halogens, —($C_3$–$C_6$) cycloalkyl, and trifluoromethoxy;

X is O, S, SO, $SO_2$, $NR_4$, C=O, CH(OH), $CHR_4$, $$-O-\overset{O}{\underset{\|}{C}}-,\ -\overset{O}{\underset{\|}{C}}-O-,\ -\overset{R_4}{\underset{|}{N}}-\overset{O}{\underset{\|}{C}}-,\ \text{or}\ -\overset{O}{\underset{\|}{C}}-\overset{R_4}{\underset{|}{N}}-;$$

m is 0, 1 or 2;

n is 0, 1 or 2;

all stereoisomers thereof; or a pharmaceutically acceptable salt thereof.

In another aspect, this invention relates to compounds of formula I wherein $R_1$ is phenyl, naphthyl, benzoxazotonyl, indolyl, indolonyl, benzimidazolyl, or quinolyl;

wherein $R_1$ and $R_3$ may be independently substituted with up to three substituents independently selected from the group consisting of fluoro, chloro, bromo, iodo, cyano, —$NR_4R_5$, —($C_1$–$C_6$)alkoxy, —$COOR_4$, —$CONR_4R_5$, —($C_1$–$C_6$)alkyl, —($C_1$–$C_6$)alkyl substituted with one to six halogens, —($C_3$–$C_6$)cycloalkyl, and trifluoromethoxy;

$R_2$ is H or $CH_3$;

X is O, C=O, CHOH, —C(=O)O—, or $CH_2$;

m is 0 or 1;

n is 0 or 1; or a pharmaceutically acceptable salt thereof.

In another aspect, this invention relates to compounds of formula I wherein $R_1$ is phenyl or substituted phenyl;

$R_3$ is substituted or unsubstituted phenyl, pyridinyl, or pyrimidinyl;

X is O, —C(=O)O—, or $CH_2$; or a pharmaceutically acceptable salt thereof.

In another aspect, this invention relates to compounds of formula I wherein $R_2$ is H;

X is O;

m is 0;

n is 1; or a pharmaceutically acceptable salt thereof.

In another aspect, this invention relates to compounds of formula I wherein $R_2$ is H;

X is O;

m is 1;

n is 0; or a pharmaceutically acceptable salt thereof.

In another aspect, this invention relates to compounds of formula I wherein $R_2$ is H;

X is —C(=O)O—;

m is 0;

n is 0; or a pharmaceutically acceptable salt thereof.

In another aspect, this invention relates to compounds of formula I wherein $R_1$ is fluorophenyl, diflurophenyl, or cyanophenyl;

$R_3$ is chloropyridinyl; or a pharmaceutically acceptable salt thereof.

In another aspect, this invention relates to compounds of formula I wherein $R_1$ is fluorophenyl, diflurophenyl, or cyanophenyl;

$R_3$ is fluoropyrimidinyl; or a pharmaceutically acceptable salt thereof.

In another aspect, this invention relates to compounds of formula I wherein $R_1$ is fluorophenyl, diflurophenyl, or cyanophenyl;

$R_3$ is chloropyridinyl; or a pharmaceutically acceptable salt thereof.

In another aspect, this invention relates to compounds of formula I wherein $R_1$ is fluorophenyl, diflurophenyl, or cyanophenyl;

$R_3$ is fluoropyrimidinyl; or a pharmaceutically acceptable salt thereof.

In another aspect, this invention relates to compounds of formula I wherein $R_1$ is fluorophenyl, diflurophenyl, or cyanophenyl;

$R_3$ is chloropyridinyl; or a pharmaceutically acceptable salt thereof.

In another aspect, this invention relates to compounds of formula I wherein $R_1$ is fluorophenyl, diflurophenyl, or cyanophenyl;

$R_3$ is fluoropyrimidinyl; or a pharmaceutically acceptable salt thereof.

In another aspect, this invention relates to compounds of formula I wherein $R_3$ is 5-chloro-pyridin-2-yl-; or a pharmaceutically acceptable salt thereof.

In another aspect, this invention relates to compounds of formula I wherein $R_3$ is 5-fluoro-pyrimidin-2-yl-; or a pharmaceutically acceptable salt thereof.

In another aspect, this invention relates to compounds of formula I wherein $R_3$ is 5-chloro-pyridin-2-yl-; or a pharmaceutically acceptable salt thereof.

In another aspect, this invention relates to compounds of formula I wherein $R_3$ is 5-fluoro-pyrimidin-2-yl-; or a pharmaceutically acceptable salt thereof.

In another aspect, this invention relates to compounds of formula I wherein $R_3$ is 5-chloro-pyridin-2-yl-; or a pharmaceutically acceptable salt thereof.

In another aspect, this invention relates to compounds of formula I wherein $R_3$ is 5-fluoro-pyrimidin-2-yl-; or a pharmaceutically acceptable salt thereof.

Preferred compounds of the invention are:

(7S,8aS)-7-(4-fluorophenoxy)methyl-2-(5-chloropyridin-2-yl)-1,2,3,4,6,7,8,8a-octahydro-pyrrolo[1,2-a]pyrazine;

(7S,8aS)-7-(3,5-difluorophenoxy)methyl-2-(5-chloropyridin-2-yl)-1,2,3,4,6,7,8,8a-octahydro-pyrrolo[1,2-a]pyrazine;

(7S,8aS)-7-(3-cyanophenoxy)methyl-2-(5-chloropyidin-2-yl)-1,2,3,4,6,7,8,8a-octahydro-pyrrolo[1,2-a]pyrazine;

(7S,8aS)-7-(4-cyanophenoxy)methyl-2-(5-chloropyidin-2-yl)-1,2,3,4,6,7,8,8a-octahydro-pyrrolo[1,2-a]pyrazine;

(7S,8aS)-7-(4-fluorobenzyl)oxy-2-(5-chloropyridin-2-yl)-1,
2,3,4,6,7,8,8a-octahydro-pyrrolo[1,2-a]pyrazine;
(7S,8aS)-2-(5-chloropyridin-2-yl)-1,2,3,4,6,7,8,8a-octahydro-pyrrolo[1,2-a]pyrazin-7-yl benzoate;
(7S,8aS)-7-(4-fluorophenoxy)methyl-2-(5-fluoropyrimidin-2-yl)-1,2,3,4,6,7,8,8a-octahydro-pyrrolo[1,2-a]pyrazine;
(7S,8aS)-7-(3,5-difluorophenoxy)methyl-2-(5-fluoropyrimidin-2-yl)-1,2,3,4,6,7,8,8a-octahydro-pyrrolo[1,2-a]pyrazine;
(7S,8aS)-7-(3-cyanophenoxy)methyl-2-(5-fluoropyrimidin-2-yl)-1,2,3,4,6,7,8,8a-octahydro-pyrrolo[1,2-a]pyrazine;
(7S,8aS)-7-(4-cyanophenoxy)methyl-2-(5-fluoropyrimidin-2-yl)-1,2,3,4,6,7,8,8a-octahydro-pyrrolo[1,2-a]pyrazine;
(7S,8aS)-7-(4-fluorobenzyl)oxy-2-(5-fluoropyrimidin-2-yl)-1,2,3,4,6,7,8,8a-octahydro-pyrrolo[1,2-a]pyrazine;
(7S,8aS)-2-(5-fluoropyrimidin-2-yl)-1,2,3,4,6,7,8,8a-octahydro-pyrrolo[1,2-a]pyrazin-7-yl benzoate;
(7S,8aS)-7-(3-cyanobenzyl)oxy-2-(5-fluoropyrimidin-2-yl)-1,2,3,4,6,7,8,8a-octahydro-pyrrolo[1,2-a]pyrazine;
and pharmaceutically acceptable salts thereof.

This invention also relates to a method for treating or preventing disorders of the dopamine system in a mammal, including a human, comprising administering to said mammal an amount of a compound according to claim 1, or a pharmaceutically acceptable salt thereof, that is effective in treating or preventing such disorder.

This invention also relates to a method for treating or preventing psychotic disorders such as affective psychosis, schizophrenia, and schizoaffective disorders in a mammal, including a human, comprising administering to said mammal an amount of a compound according to claim 1, or a pharmaceutically acceptable salt thereof, that is effective in treating or preventing such disorder.

This invention also relates to a method for treating or preventing movement disorders such as extrapyramidal side effects from neuroleptic agents, neuroleptic malignant syndrome, tardive dyskinesia, or Gilles De La Tourette's syndrome in a mammal, including a human, comprising administering to said mammal an amount of a compound according to claim 1, or a pharmaceutically acceptable salt thereof, that is effective in treating or preventing such disorder.

This invention also relates to a method for treating or preventing movement disorders such as Parkinson's disease or Huntington's disease in a mammal, including a human, comprising administering to said mammal an amount of a compound according to claim 1, or a pharmaceutically acceptable salt thereof, that is effective in treating or preventing such disorder.

This invention also relates to a method for treating or preventing gastrointestinal disorders such as gastric acid secretion in a mammal, including a human, comprising administering to said mammal an amount of a compound according to claim 1, or a pharmaceutically acceptable salt thereof, that is effective in treating or preventing such disorder.

This invention also relates to a method for treating or preventing gastrointestinal disorders such as emesis in a mammal, including a human, comprising administering to said mammal an amount of a compound according to claim 1, or a pharmaceutically acceptable salt thereof, that is effective in treating or preventing such disorder.

This invention also relates to a method for treating or preventing chemical abuse, chemical dependencies or substance abuse in a mammal, including a human, comprising administering to said mammal an amount of a compound according to claim 1, or a pharmaceutically acceptable salt thereof, that is effective in treating or preventing such disorder.

This invention also relates to a method for treating or preventing vascular and cardiovascular disorders such as congestive heart failure and hypertension in a mammal, including a human, comprising administering to said mammal an amount of a compound according to claim 1, or a pharmaceutically acceptable salt thereof, that is effective in treating or preventing such disorder.

This invention also relates to a method for treating or preventing ocular disorders in a mammal, including a human, comprising administering to said mammal an amount of a compound according to claim 1, or a pharmaceutically acceptable salt thereof, that is effective in treating or preventing such disorder.

This invention also relates to a method for treating or preventing sleep disorders in a mammal, including a human, comprising administering to said mammal an amount of a compound according to claim 1, or a pharmaceutically acceptable salt thereof, that is effective in treating or preventing such disorder.

This invention also relates to a pharmaceutical composition for treating or preventing disorders of the dopamine system in a mammal, including a human, comprising administering to said mammal an amount of a compound according to claim 1, or a pharmaceutically acceptable salt thereof, that is effective in treating or preventing such disorder.

This invention also relates to a pharmaceutical composition for treating or preventing psychotic disorders such as affective psychosis, schizophrenia, and schizoaffective disorders in a mammal, including a human, comprising administering to said mammal an amount of a compound according to claim 1, or a pharmaceutically acceptable salt thereof, that is effective in treating or preventing such disorder.

This invention also relates to a pharmaceutical composition for treating or preventing movement disorders such as extrapyramidal side effects from neuroleptic agents, neuroleptic malignant syndrome, tardive dyskinesia, or Gilles De La Tourette's syndrome in a mammal, including a human, comprising administering to said mammal an amount of a compound according to claim 1, or a pharmaceutically acceptable salt thereof, that is effective in treating or preventing such disorder.

This invention also relates to a pharmaceutical composition for treating or preventing movement disorders such as Parkinson's disease or Huntington's disease in a mammal, including a human, comprising administering to said mammal an amount of a compound according to claim 1, or a pharmaceutically acceptable salt thereof, that is effective in treating or preventing such disorder.

This invention also relates to a pharmaceutical composition for treating or preventing gastrointestinal disorders such as gastric acid secretion in a mammal, including a human, comprising administering to said mammal an amount of a compound according to claim 1, or a pharmaceutically acceptable salt thereof, that is effective in treating or preventing such disorder.

This invention also relates to a pharmaceutical composition for treating or preventing gastrointestinal disorders such as emesis in a mammal, including a human, comprising administering to said mammal an amount of a compound according to claim 1, or a pharmaceutically acceptable salt thereof, that is effective in treating or preventing such disorder.

This invention also relates to a pharmaceutical composition for treating or preventing chemical abuse, chemical dependencies or substance abuse in a mammal, including a human, comprising administering to said mammal an amount of a compound according to claim 1, or a pharmaceutically acceptable salt thereof, that is effective in treating or preventing such disorder.

This invention also relates to a pharmaceutical composition for treating or preventing vascular and cardiovascular disorders such as congestive heart failure and hypertension in a mammal, including a human, comprising administering to said mammal an amount of a compound according to claim 1, or a pharmaceutically acceptable salt thereof, that is effective in treating or preventing such disorder.

This invention also relates to a pharmaceutical composition for treating or preventing ocular disorders in a mammal, including a human, comprising administering to said mammal an amount of a compound according to claim 1, or a pharmaceutically acceptable salt thereof, that is effective in treating or preventing such disorder.

This invention also relates to a pharmaceutical composition for treating or preventing sleep disorders in a mammal, including a human, comprising administering to said mammal an amount of a compound according to claim 1, or a pharmaceutically acceptable salt thereof, that is effective in treating or preventing such disorder.

In another aspect, this invention relates to compounds of formula IV

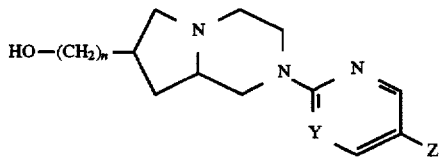

IV wherein n is 0 or 1;

Y is CH or N;

Z is chloro or fluoro;

all stereoisomers thereof;

which are useful intermediates for the preparation of compounds of formula I.

Preferred compounds of formula IV, which are useful intermediates for the preparation of compounds of formula I, are:

(7S,8aS)-7-hydroxymethyl-2-(5-chloropyridin-2-yl)-1,2,3,4,6,7,8,8a-octahydro-pyrrolo[1,2-a]pyrazine, (7S,8aS)-7-hydroxymethyl-2-(5-fluoropyrimidin-2-yl)-1,2,3,4,6,7,8,8a-octahydro-pyrrolo[1,2-a]pyrazine, (7R,8aS)-7-hydroxy-2-(5-chloropyridin-2-yl)-1,2,3,4,6,7,8,8a-octahydro-pyrrolo[1,2-a]pyrazine, (7R,8aS)-7-hydroxy-2-(5-fluoropyrimidin-2-yl)-1,2,3,4,6,7,8,8a-octahydro-pyrrolo[1,2-a]pyrazine, (7S,8aS)-7-hydroxy-2-(5-chloropyridin-2-yl)-1,2,3,4,6,7,8,8a-octahydro-pyrrolo[1,2-a]pyrazine, and (7S,8aS)-7-hydroxy-2-(5-fluoropyrimidin-2-yl)-1,2,3,4,6,7,8,8a-octahydro-pyrrolo[1,2-a]pyrazine.

This invention also relates to the pharmaceutically acceptable acid addition salts of compounds of the formula I. The compounds of formula I are basic in nature and are capable of forming a wide variety of salts with various inorganic and organic acids. The acids that may be used to prepare pharmaceutically acceptable acid addition salts of those compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, fumarate, gluconate, glucaronate, saccharate, formate, benzoate, glutamate, methanesulfonate, ethanesulfonate, benzenesulfonate, and p-toluenesulfonate.

The term "one or more substituents", as used herein, includes from one to the maximum number of substituents possible based on the number of available bonding sites.

The chemist of ordinary skill will recognize that certain combinations of substituents may be chemically unstable and will avoid these combinations or alternatively protect sensitive groups with well known protecting groups.

The term "alkyl", as used herein, unless otherwise indicated, includes saturated monovalent hydrocarbon radicals having straight, branched or cyclic moieties or combinations thereof.

The term "alkoxy", as used herein, unless otherwise indicated, refers to radicals having the formula —O-alkyl, wherein "alkyl" is defined as above.

The compounds of formula I contain chiral centers and therefore exist in different enantiomeric forms. This invention relates to all stereoisomers of compounds of the formula I and mixtures thereof.

The term "disorders of the dopamine system", as referred to herein, refers to disorders the treatment or prevention of which can be effected or facilitated by altering (i.e., increasing or decreasing) dopamine mediated neurotransmission.

The compounds in accordance with the present invention, being ligands for dopamine receptor subtypes, especially the dopamine $D_4$ receptor, within the body, are accordingly of use in the treatment or prevention of disorders of the dopamine system.

It is generally accepted knowledge that dopamine receptors are important for many functions in the animal body. For example, altered functions of these receptors participate in the genesis of psychosis, addiction, sleep, feeding, learning, memory, sexual behavior, and blood pressure.

This invention provides dopamine ligands that are of use in the treatment and/or prevention of disorders of the dopamine system, including schizophrenia, nausea, Parkinson's disease, tardive dyskinesias and extrapyramidal side-effects associated with treatment by conventional neuroleptic agents, neuroleptic malignant syndrome, and disorders of hypothalamic-pituitary function such as hyperprolactinaemia and amenorrhoea.

Upper gastrointestinal tract motility is believed to be under the control of the dopamine system. The compounds according to the present invention are of use in the prevention or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, are accordingly of value in the prevention or reduction of dependence on a dependence-inducing agent.

Dopamine is known to be a peripheral vasodilator; for example, it has been shown to exert a dilatory effect on the renal vascular bed. This shows that the compounds of the present invention are beneficial in controlling vascular blood flow.

The localization of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention are of assistance in the prevention or treatment of such conditions as hypertension and congestive heart failure.

The presence of D4 receptor mRNA in rat retina has been noted (Cohen, et al. *Proc. Nat. Acad. Sci.*, 1992, 89, 12093), suggesting that dopamine and D4 receptors play a role in ocular function. The compounds of this invention may therefore be useful in the treatment of ocular disorders. Furthermore, D4 receptors influence melatonin biosynthesis in chick retina (Zawilska, Nowak, *Neuroscience Lett.*, 1994, 166, 203), and since melatonin has been used for the treatment of sleep disorders, the compounds of this invention may be useful for the treatment of sleep disorders as well.

DETAILED DESCRIPTION OF THE INVENTION

The compounds of formula I are readily prepared by methods which are summarized in the Schemes.

While the overall routes and various intermediates in the Schemes are novel, the individual chemical steps are generally analogous to known chemical transformations. Generally suitable conditions are found in the prior art. Isolation and purification of the products is accomplished by standard procedures which are known to a chemist of ordinary skill. Particularly well-suited conditions are exemplified below.

As used herein, the expression "reaction inert solvent" refers to a solvent system in which the components do not interact with starting materials, reagents, intermediates of products in a manner which adversely affects the yield of the desired product.

During any of the following synthetic sequences it may be necessary and/or desirable to protect sensitive or reactive groups on any of the molecules concerned. This may be achieved by means of conventional protecting groups, such as those described in T. W. Greene, *Protective Groups in Organic Chemistry*, John Wiley & Sons, 1981; and T. W. Greene and P. G. M. Wuts, *Protective Groups in Organic Chemistry*, John Wiley & Sons, 1991.

The expression "nitrogen protecting group" as used herein means a moiety which when coupled with a basic nitrogen will remain inert while other reactions are carried out. The nitrogen protecting group may then be removed under mild conditions yielding the free amino group. This invention contemplates two types of nitrogen protecting groups: those which may be removed by treatment with strong acid and those which may be removed by hydrogenation.

Examples of nitrogen protecting groups removed by strong acid are tert-butoxycarbonyl, methoxycarbonyl, ethoxycarbonyl, trimethylsilylethoxycarbonyl, 1-adamantyloxycarbonyl, vinyloxycarbonyl, diphenylmethoxycarbonyl, trityl, acetyl and benzoyl.

Examples of nitrogen protecting groups removed by hydrogenation are benzyloxycarbonyl, 9-fluorenylmethyloxycarbonyl, 2-phenylethyloxycarbonyl, benzyl, p-methoxybenzyloxycarbonyl, and p-nitrobenzyloxycarbonyl. A preferred nitrogen protecting group is benzyl.

Compounds of formula VII are useful intermediates for the preparation of compounds of formula I. Compounds of formula VII wherein n is 0 are known (Diafi, L.; et al. *J. Het. Chem.*, 1990, 27, 2181). Compounds of formula VII wherein n is 1 may be prepared according to Scheme 1. Compounds of formula VII wherein n is 2 may be prepared according to Scheme 2.

Scheme 1 summarizes methods suitable for preparing compounds VII wherein n is 1. Compounds of the formulas V and VI wherein $R_2$ is hydrogen or methyl are known (Jones, R. C. F.; Howard, K. J. *J. Chem. Soc. Perkin Trans. 1*, 1993, 2391), and additional examples of VII wherein $R_2$ is a straight chain, branched or cyclic $C_1$ to $C_6$ alkyl may be prepared by this method using acrylate esters where the $R_2$ substituent is placed at the 2-position of the acrylate starting material. Compounds VI may be converted into VII by the action of a strong hydride reducing agent in a reaction inert solvent, preferably an ether such as tetrahydrofuran (THF), 1,4-dioxane or 1,2-dimethoxyethane at a temperature from about 0° C. to about 100° C., preferably from about 25° C. to about 65° C. Many suitable reducing agents are known, particularly hydrides of aluminum and boron, and lithium aluminum hydride or diborane are preferred reducing agents. Compounds VII prepared by this method may be produced as a mixture of stereoisomers, and the stereoisomers are separated by chromatographic methods known to a chemist of ordinary skill.

Compound V wherein $R_2$ is hydrogen may be used to prepare VIII by the action of a base in a lower alcohol solvent such as methanol, ethanol or propanol with an amine base, wherein 1,8-diazbicyclo[5.4.0]undec-7-ene (DBU) or 1,5-diazbicyclo[4.3.0]non-5-ene (DBN) are preferred bases, at a temperature from about 0° C. to about 100° C., where a preferred temperature is from about 20° C. to about 60° C. Reduction of VIII to IX may be accomplished by exposing a mixture of VIII and a noble metal catalyst, wherein palladium is a preferred noble metal catalyst, wherein the metal may be conveniently suspended on an inert solid support such as charcoal, in a solvent such as ethyl acetate or hexane or a mixture thereof, to an atmosphere of hydrogen gas at a pressure of about 1 to 100 atmospheres, where a preferred pressure of hydrogen gas is about one to about ten atmospheres. Compound IX may be converted into VII by the action of a strong hydride reducing agent in a reaction inert solvent, preferably an ether such as tetrahydrofuran (THF), 1,4-dioxane or 1,2-dimethoxyethane at a temperature from about 0° C. to about 100° C., preferably from about 25° C. to about 65° C. Many suitable reducing agents are known, particularly hydrides of aluminum and boron, and lithium aluminum hydride or diborane are preferred reducing agents. Compounds VII prepared by this method may be produced as a mixture of stereoisomers, and the stereoisomers are separated by chromatographic methods known to a chemist of ordinary skill.

Compound IX may be converted into compound VI by treating a solution of IX in an ether solvent, preferably tetrahydrofuran (THF), with an alkali metal amide base, preferably lithium diisopropylamide or potassium hexamethyl disilazide, at a temperature from about 0° C. to about −100° C., preferably from about −50° C. to about −80° C., followed by addition of an appropriate alkylating agent, such as an alkyl halide, wherein alkyl halides of one to six carbon atoms and bromide or iodide are preferred. Compound IX prepared by this method may be converted into VII by the action of a strong hydride reducing agent in a reaction inert solvent, preferably an ether such as tetrahydrofuran (THF), 1,4-dioxane or 1,2-dimethoxyethane at a temperature from about 0° C. to about 100° C., preferably from about 25° C. to about 65° C. Many suitable reducing agents are known, particularly hydrides of aluminum and boron, and lithium aluminum hydride or diborane are preferred reducing agents.

Referring to Scheme 2, compounds of formula VII wherein n is 2 may be prepared from compounds VII where n is 1 by first treating compound VII (n=1) with an alkyl- or aryl-sulfonyl chloride, where methane sulfonyl chloride or tolyl sulfonyl chloride are preferred, in a reaction inert solvent, where methylene chloride or chloroform are preferred, at a temperature from about −10° C. to about 20°

C. in the presence of a trialkyl amine base, where triethyl amine or diisopropyl ethyl amine are preferred. Treatment of the alkyl- or aryl-sulfonyl ester thus formed with an alkali metal salt of cyanide, where potassium cyanide is preferred, in a polar solvent, where dimethylformamide (DMF) or dimethyl sulfoxide (DMSO) are preferred, at a temperature from about 20° C. to about 100° C., where 50° C. to 80° C. is preferred, is a method that may be used to produce X. Conversion of nitrile X into aldehyde XI may be accomplished by treating a solution of X in an ether solvent, preferably tetrahydrofuran (THF), with a hydride reducing agent, preferably diisobutyl aluminum hydride, at a temperature from about 0° C. to about 80° C., preferably from about 20° C. to about 60° C. Many reagents capable of reducing aldehyde XI to alcohol VII where n is 2 are known, and this transformation may be conveniently accomplished by using a hydride of boron, preferably sodium borohydride or sodium cyanoborohydride, in a lower alcohol solvent, preferably methanol or ethanol, at a temperature from about –10° C. to about 30° C.

Scheme 3 summarizes methods for preparing compounds I from compounds VII wherein X is O, S, NR$_4$, C(=O)O, C(=O)NR$_4$ or CHR$_4$.

Referring to Scheme 3, a method for coupling alcohols VII with compounds of the formula R$_1$—(CH$_2$)$_m$—XH wherein X is O, S, NR$_4$, C(=O)O or C(=O)NR$_4$ to produce XII involves conversion of the alcohol moiety of VII into a leaving group such as lower-alkylsulfonyl ester or arylsulfonyl ester as the first step of a two-step process. The alkylo or arylsulfonyl ester is first prepared by the reaction of an alkyl- or arylsulfonyl chloride with alcohol VII in the presence of a trialkyl amine, preferably triethylamine, in a reaction inert solvent, preferably methylene chloride or chloroform, at a temperature from about –10° C. to about 30° C. In a second step, a compound of formula R$_1$—(CH$_2$)$_m$—XH wherein X is O, S, NR$_4$, C(=O)O or (C=O)NR$_4$, is combined with a suitable base such as an alkali metal hydride, preferably sodium hydride, or an alkali metal carbonate, preferably sodium carbonate or potassium carbonate, and the alkyl- or arylsulfonyl derivative of VII in a polar reaction inert solvent, preferably dimethyl formamide (DMF) or dimethylsulfoxide (DMSO), at a temperature from about 0° C. to about 150° C., preferably from about 50° C. to about 100° C.

In the case wherein X is O or S and m is 0, compounds XII may be prepared from VII by combining approximately equimolar quantities of VII, an alcohol of formula R$_1$OH or a thiol of formula R$_1$SH, triarylphosphine, preferably triphenylphosphine (Ph$_3$P), and dialkyl azodicarboxylate, preferably diethyl azodicarboxylate (DEAD), in a relatively polar ether solvent such as tetrahydrofuran (THF), 1,4-dioxane or 1,2-dimethoxyethane at a temperature from about 0° C. to about 100° C., preferably from about 25° C. to about 60° C.

Compounds XII wherein X is C(=O)O may be conveniently prepared by reacting VII with a carboxylic acid halide of the formula R$_1$(CH$_2$)$_m$C(=O)Y, wherein Y is a halogen atom, preferably chloro, in a reaction inert solvent, preferably methylene chloride or chloroform, accompanied by a mild base, preferably triethylamine, 4-(dimethylamino) pyridine, or pyridine, at a temperature from about –10° C. to about 35° C. In another preferred method, compound XII may be prepared by combining VII with a compound of the formula R$_1$(CH$_2$)$_m$CO$_2$H, a triarylphosphine, preferably triphenylphosphine (Ph$_3$P), and dialkyl azodicarboxylate, preferably diethyl azodicarboxylate (DEAD), in a relatively polar ether solvent, preferably tetrahydrofuran (THF), 1,4-dioxane or 1,2-dimethoxyethane, at a temperature from about 0° C. to about 100° C., preferably from about 25° C. to about 60° C.

In the case wherein X is O and m is 1 or 2, XII may be conveniently prepared by reacting VII with a compound of formula R$_1$—(CH$_2$)$_m$—L wherein L is a leaving group and a suitable base such as an alkali metal hydride, preferably sodium hydride, or an alkali metal carbonate, preferably sodium carbonate or potassium carbonate, in a reaction inert solvent, preferably a polar solvent such as dimethylformamide (DMF), dimethyl sulfoxide (DMSO) or acetonitrile, at a temperature from about 0° C. to about 100° C., preferably from about 25° C. to about 60° C. The term "leaving group" refers to groups which may be replaced by other groups under suitable conditions, and includes, for example, halogen, lower-alkylsulfonyl and arylsulfonyl. Methanesulfonyl, bromo or iodo are preferred leaving groups.

A method of preparing compounds of formula XII wherein X is CHR$_4$ from VII involves conversion of the alcohol moiety of VII into a leaving group such as lower-alkylsulfonyl ester or arylsulfonyl ester as the first step of a two-step process. The alkyl- or arylsulfonyl ester is first prepared by the reaction of an alkyl- or arylsulfonyl chloride with VII in the presence of a trialkyl amine, preferably triethylamine, in a reaction inert solvent, preferably methylene chloride or chloroform, at a temperature from about –10° C. to about 30° C. In a second step, the alkyl- or arylsulfonyl derivative is combined with a compound of the formula R$_1$(CH$_2$)$_m$CH(R$_4$)MgY wherein Y is a halogen atom, preferably chloro, bromo, or iodo, and a salt of copper(I), preferably cuprous bromide or cuprous iodide, in an ether solvent, preferably tetrahydrofuran (THF), 1,4-dioxane or 1,2-dimethoxyethane, at a temperature from about –100° C. to about 50° C., preferably from about –80° C. to about 25° C.

Compounds of formula XII may be converted into compounds XIII by combining XII with a noble metal catalyst on an inert solid material, preferably palladium on charcoal, in a polar solvent such as a lower alcohol, preferably methanol or ethanol, to an atmosphere of hydrogen gas at a pressure of about one to twenty atmospheres and a temperature from about 0° C. to about 100° C., preferably from about 25° C. to about 60° C. Alternately, XIII may be conveniently prepared from XII by the action of ammonium formate and a noble metal catalyst, preferably palladium on charcoal, in a polar solvent such as water or a lower alcohol, preferably methanol or ethanol, or a mixture of water and a lower alcohol, at a temperature from about 0° C. to about 100° C., preferably from about 25° C. to about 60° C.

Compounds of formula I may be prepared from compounds of formula XIII using methods which are directly analogous to those described by Bright and Desai (U.S. Pat. No. 5,122,525). The term "activated form of R$_3$" means a chemical derivative of R$_3$ having the formula

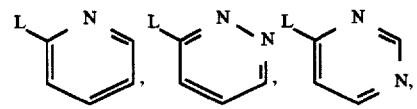

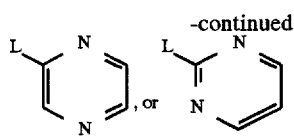

wherein L is a leaving group. The term "leaving group" (L) refers to groups which may be replaced by other groups under suitable conditions, and include, for example, halogen, lower-alkylsulfonyl and arylsulfonyl. Activated forms of $R_3$ may also be derivatives of benzene bearing an electron withdrawing group (EWG) and a leaving group (L) in the ortho- or para- positions relative to one other:

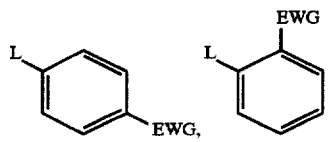

Where the activated form of $R_3$ is a derivative of benzene, halogens are the preferred leaving groups, especially fluoro, and nitro or cyano are examples of preferred electron withdrawing groups. The reaction of compound XIII with an activated form of $R_3$ to form I is conveniently carried out in reaction inert solvents such as water, $C_1$–$C_6$ alcohols, or dimethyl sulfoxide, wherein water, propanol, butanol, or pentanol are preferred, at a temperature from about 30° C. to about 170° C., preferably from about 60° C. to about 110° C. The presence of an acid acceptor such as a trialkyl amine or an alkali carbonate may be useful, and sodium carbonate or potassium carbonate is preferred.

Compounds of formula I wherein X is O, S, $NR_4$, C(=O) O, C(=O)$NR_4$ or $CHR_4$ may also be prepared from VII by first removing the benzyl nitrogen protecting group. The formation of amino alcohols XIV from VII by this method may be conveniently carried out by combining VII with a noble metal catalyst on an inert solid material, preferably palladium on charcoal, in a polar solvent such as a lower alcohol, preferably methanol or ethanol, to an atmosphere of hydrogen gas at a pressure of about one to twenty atmospheres and a temperature from about 0° C. to about 100° C., preferably from about 25° C. to about 60° C. Alternately, XIV may be conveniently prepared from VII by the action of ammonium formate and a noble metal catalyst, preferably palladium on charcoal, in a polar solvent such as water or a lower alcohol, preferably methanol or ethanol, or a mixture of water and a lower alcohol, at a temperature from about 0° C. to about 100° C., preferably from about 25° C. to about 60° C.

Compounds XV may be prepared by reacting XIV with an activated form of $R_3$ in a reaction inert solvent such as water, $C_1$–$C_6$ alcohols, or dimethyl sulfoxide, wherein water, propanol, butanol, or pentanol are preferred, at a temperature from about 30° C. to about 170° C., preferably from about 60° C. to about 110° C. The presence of an acid acceptor such as a trialkyl amine or an alkali carbonate may be useful, and sodium carbonate or potassium carbonate are preferred.

A useful method for coupling alcohols XV with compounds of the formula $R_1$—$(CH_2)_m$—XH wherein X is O, S, $NR_4$, (C=O)O or C(=O)$NR_4$ to produce I involves conversion of the alcohol moiety of XV into a leaving group such as lower-alkylsulfonyl ester or arylsulfonyl ester as the first step of a two-step process. The alkyl- or arylsulfonyl ester is first prepared by the reaction of an alkyl- or aryl-sulfonyl chloride with alcohol XV in the presence of a trialkyl amine, preferably triethylamine, in a reaction inert solvent, preferably methylene chloride or chloroform, at a temperature from about −10° C. to about 30° C. In a second step, a compound of formula $R_1$—$(CH_2)_m$—XH wherein X is O, S, $NR_4$, (C=O)O or C(=O)$NR_4$ is combined with a suitable base such as an alkali metal hydride, preferably sodium hydride, or an alkali metal carbonate, preferably sodium carbonate or potassium carbonate, and the alkyl- or arylsulfonyl derivative of XV in a polar reaction inert solvent, preferably dimethyl formamide (DMF) or dimethylsulfoxide (DMSO), at a temperature from about 0° C. to about 150° C., preferably from about 50° C. to about 100° C.

In the case wherein X is O or S and m is 0, compounds I may be prepared from XV by combining approximately equimolar quantities of XV, an alcohol of formula $R_1$OH or a thiol of formula $R_1$SH, triarylphosphine, preferably triphenylphosphine ($Ph_3P$), and dialkyl azodicarboxylate, preferably diethyl azodicarboxylate (DEAD), in a relatively polar ether solvent such as tetrahydrofuran (THF), 1,4-dioxane or 1,2-dimethoxyethane at a temperature from about 0° C. to about 100° C., preferably from about 25° C. to about 60° C.

Compounds I wherein X is O and m is 1 or 2, may be conveniently prepared by reacting XV with a compound of formula $R_1$—$(CH_2)_m$—L wherein L is a leaving group and a suitable base such as an alkali metal hydride, preferably sodium hydride, or an alkali metal carbonate, preferably sodium carbonate or potassium carbonate, in a reaction inert solvent, preferably a polar solvent such as dimethylformamide (DMF), dimethyl sulfoxide (DMSO) or acetonitrile at a temperature from about 0° C. to about 100° C., preferably from about 25° C. to about 60° C. The term "leaving group" refers to groups which may be replaced by other groups under suitable conditions, and include, for example, halogen, lower-alkylsulfonyl and arylsulfonyl. Methanesulfonyl, bromo or iodo are preferred leaving groups.

Compounds I wherein X is C(=O)O may be conveniently prepared by reacting XV with a carboxylic acid halide of the formula $R_1$$(CH_2)_m$C(=O)Y, wherein Y is a halogen atom, preferably chloro, in a reaction inert solvent, preferably methylene chloride or chloroform, accompanied by a mild base, preferably triethylamine, 4-(dimethylamino)pyridine, or pyridine, at a temperature from about −10° C. to about 35° C. In another preferred method, compound I may be prepared by combining XV with a compound of the formula $R_1(CH_2)_mCO_2H$, a triarylphosphine, preferably triphenylphosphine ($Ph_3P$), and dialkyl azodicarboxylate, preferably diethyl azodicarboxylate (DEAD), in a relatively polar ether solvent, preferably tetrahydrofuran (THF), 1,4-dioxane or 1,2-dimethoxyethane, at a temperature from about 0° C. to about 100° C., preferably from about 25° C. to about 60° C.

Compounds I wherein X is C(=O)N($R_4$) may be conveniently prepared by conversion of the alcohol moiety of XV into a leaving group such as lower-alkylsulfonyl ester or arylsulfonyl ester as the first step of a two-step process. The alkyl- or arylsulfonyl ester is first prepared by the reaction of an alkyl- or arylsulfonyl chloride with XV in the presence of a trialkyl amine, preferably triethylamine, in a reaction inert solvent, preferably methylene chloride or chloroform, at a temperature from about −10° C. to about 30° C. In a second step, the alkyl- or arylsulfonyl derivative is combined with a compound of the formula $R_1(CH_2)_mC(=O)$$NHR_4$, and a base, preferably sodium hydride or potassium carbonate, in a polar solvent, preferably dimethyl formamide (DMF) or dimethyl sulfoxide (DMSO), at a temperature from about 0° C. to about 100° C., preferably from about 25°

C. to about 60° C. In cases wherein $R_4$ is hydrogen, treating compound I wherein X is C(=O)NH with a compound of formula $R_4$—L, wherein L is a leaving group, preferably chloro, bromo, iodo, lower-alkylsulfonyl ester or arylsulfonyl ester, and a base, preferably sodium hydride, in a polar reaction inert solvent, preferably dimethyl formamide (DMF) or dimethyl sulfoxide (DMSO), at a temperature from about 0° C. to about 100° C., preferably from about 25° C. to about 60° C., is another preferred method for preparing compounds of formula I wherein X is C(=O)N($R_4$).

A method of preparing compounds of formula I wherein X is CH$R_4$ from XV involves conversion of the alcohol moiety of XV into a leaving group such as lower-alkylsulfonyl ester or arylsulfonyl ester as the first step of a two-step process. The alkyl- or arylsulfonyl ester is first prepared by the reaction of an alkyl- or arylsulfonyl chloride with XV in the presence of a trialkyl amine, preferably triethylamine, in a reaction inert solvent, preferably methylene chloride or chloroform, at a temperature from about −10° C. to about 30° C. In a second step, the alkyl- or arylsulfonyl derivative is combined with a compound of the formula $R_1(CH_2)_m CH(R_4)MgY$ wherein Y is a halogen atom, preferably chloro, bromo, or iodo, and a salt of copper(I), preferably cuprous bromide or cuprous iodide, in an ether solvent, preferably tetrahydrofuran (THF), 1,4-dioxane or 1,2-dimethoxyethane, at a temperature from about −100° C. to about 50° C., preferably from about −80° C. to about 25° C.

Scheme 4 summarizes methods suitable for preparing compounds I wherein X is C(=O), CH(OH) or CH$R_4$.

A method for preparing compounds XVI from XV involves conversion of the alcohol moiety of XV into a leaving group such as lower-alkylsulfonyl ester or arylsulfonyl ester as the first step of a two-step process. The alkyl- or arylsulfonyl ester is first prepared by the reaction of an alkyl- or arylsulfonyl chloride with XV in the presence of a trialkyl amine, preferably triethylamine, in a reaction inert solvent, preferably methylene chloride or chloroform, at a temperature from about −10° C. to about 30° C. In a second step, the alkyl- or arylsulfonyl derivative is combined with an alkali metal cyanide, preferably sodium cyanide or potassium cyanide, in a polar, reaction inert solvent, preferably dimethylformamide (DMF) or dimethyl sulfoxide (DMSO), at a temperature from about 25° C. to about 100° C., preferably from about 35° C. to about 70° C.

Compounds of formula I wherein X is C(=O) may be prepared by treating XVI with a compound of the formula $R_1(CH_2)_m$—MgY wherein Y is a halogen atom, preferably chloro, bromo or iodo, in an ether solvent, preferably tetrahydrofuran (THF) or diethyl ether, at a temperature from about −30° C. to about 60° C., preferably from about −10° C. to about 30° C. Hydrolysis of the reaction mixture in a second step with a dilute aqueous solution of a strong inorganic acid, preferably hydrochloric acid or sulfuric acid, may be beneficial.

Many reagents capable of reducing compounds I wherein X is C(=O) to compounds I wherein X is CH(OH) are known, and this transformation may be conveniently accomplished by using a hydride of boron, preferably sodium borohydride, in a lower alcohol solvent, preferably methanol or ethanol, at a temperature from about −10° C. to about 30° C.

A method for preparing compounds I wherein X is CH($R_4$) from I wherein X is CH(OH) involves conversion of the alcohol moiety of I wherein X is CH(OH) into a leaving group such as lower-alkylsulfonyl ester or arylsulfonyl ester as the first step of a two-step process. The alkyl- or arylsulfonyl ester is first prepared by the reaction of an alkyl- or arylsulfonyl chloride with I wherein X is CH(OH) in the presence of a trialkyl amine, preferably triethylamine, in a reaction inert solvent, preferably methylene chloride or chloroform, at a temperature from about −10° C. to about 30° C. In a second step, the alkyl- or arylsulfonyl derivative is combined with a compound of the formula $R_4$-MgY wherein Y is a halogen atom, preferably chloro, bromo, or iodo, and a salt of copper(I), preferably cuprous bromide or cuprous iodide, in an ether solvent, preferably tetrahydrofuran (THF), 1,4-dioxane or 1,2-dimethoxyethane, at a temperature from about −100° C. to about 50° C., preferably from about −80° C. to about 25° C.

Scheme 5 summarizes methods suitable for preparing compounds of formula I wherein X is OC(=O) or N($R_4$)C(=O).

Compounds XVII may be prepared by treating XVI with an aqueous solution of a strong inorganic acid, preferably hydrochloric acid or sulfuric acid, at a temperature from about 20° C. to about 120° C., preferably from about 50° C. to about 100° C.

Many methods are known which are suitable for coupling carboxylic acids of formula XVII with alcohols of the formula $R_1(CH_2)_m$—OH to form compounds I wherein X is OC(=O). In a preferred method, a carboxylic acid of formula XVII, an alcohol of formula $R_1(CH_2)_m$—OH, a tertiary amine, preferably triethyl amine, diisopropyl ethyl amine or 4-(dimethyamino)pyridine, and 1-hydroxybenzotriazole hydrate (HOBT) dissolved in a reaction inert solvent, preferably methylene chloride or chloroform, is treated with 1-(3-dimethylaminopropyl)-3-ethylcarbodiimide hydrochloride (DEC) at a temperature from about 0° C. to about 50° C., preferably from about 10° C. to about 30° C.

Many methods are known which are suitable for coupling carboxylic acids of formula XVII with amines of the formula $R_1(CH_2)_m$—NH$R_4$ to form compounds I wherein X is N($R_4$)C(=O). In a preferred method, a carboxylic acid of formula XVII, an amine of formula $R_1(CH_2)_m$—NH$R_4$, a tertiary amine, preferably triethyl amine or diisopropyl ethyl amine, and 1-hydroxybenzotriazole hydrate (HOBT) dissolved in a reaction inert solvent, preferably methylene chloride or chloroform, is treated with 1-(3-dimethylaminopropyl)-3-ethylcarbodiimide hydrochloride (DEC) at a temperature from about 0° C. to about 50° C., preferably from about 10° C. to about 30° C. In cases wherein $R_4$ is hydrogen, treating compound I wherein X is NHC(=O) with a compound of formula $R_4$—L, wherein L is a leaving group, preferably chloro, bromo, iodo, lower-alkylsulfonyl ester or arylsulfonyl ester, and a base, preferably sodium hydride, in a polar reaction inert solvent, preferably dimethyl formamide (DMF) or dimethyl sulfoxide (DMSO), at a temperature from about 0° C. to about 100° C., preferably from about 25° C. to about 60° C., is another preferred method for preparing compounds of formula I wherein X is N($R_4$)C(=O).

Scheme 6 summarized methods for preparing compound XIV wherein n is 1 and $R_2$ is hydrogen.

Methods for preparing the stereoisomers of compound XVIII have been reported by Bridges, et al. (*J. Med. Chem.*, 1991, 34, 717). The formation of amine XIX from XVIII may be conveniently carried out by combining XVIII with a noble metal catalyst on an inert solid material, preferably palladium on charcoal, in a polar solvent such as a lower alcohol, preferably methanol or ethanol, under an atmosphere of hydrogen gas at a pressure of about one to twenty atmospheres and a temperature from about 0° C. to about 100° C., preferably from about 25° C. to about 60° C. Alternately, XIX may be conveniently prepared from XVIII by the action of ammonium formate and a noble metal catalyst, preferably palladium on charcoal, in a polar solvent such as water or a lower alcohol, preferably methanol or ethanol, or a mixture of water and a lower alcohol, at a temperature from about 1° C. to about 100° C., preferably from about 25° C. to about 60° C.

A preferred method for preparing compound XX from compound XIX involves combining 2-(phthalimido) acetaldehyde with compound XIX, an alkali metal salt of a carboxylic acid, preferably sodium acetate or sodium propionate, and a boron hydride reducing agent, preferably sodium (triacetoxy)borohydride, in a reaction inert solvent, preferably methylene chloride or chloroform, at a temperature from about 5° C. to about 30° C. in the first step of a two step process. In the second step, the 2-(phthalimido)ethyl derivative thus formed is combined with a primary amine capable of causing the removal of the phthalimido protecting group, preferably hydrazine hydrate or methyl amine, in water or a lower alcohol solvent, preferably water, methanol, or ethanol, or a mixture thereof, at a temperature from about 0° C. to about 60° C., preferably from about 5° C. to about 30° C.

Compound XX is converted into XIV wherein n is 1 by the action of a strong hydride reducing agent in a reaction inert solvent, preferably an ether such as tetrahydrofuran (THF), 1,4-dioxane or 1,2-dimethoxyethane at a temperature from about 0° C. to about 100° C., preferably from about 25° C. to about 65° C. Many suitable reducing agents are known, particularly hydrides of aluminum and boron, and lithium aluminum hydride or diborane are preferred reducing agents.

Compounds I wherein X is S may be converted into compounds I wherein X is SO by the action with an oxidizing agent, preferably about one molar equivalent of m-chloroperoxybenzoic acid, in a reaction inert solvent, preferably methylene chloride or chloroform, at a temperature from about −100° C. to about 0° C., preferably from about −80° C. to about −20° C.

Compounds I where X is S or SO may be converted into compounds I where X is $SO_2$ by the action with an oxidizing agent, preferably m-chloroperoxybenzoic acid, in reaction inert solvent, preferably methylene chloride or chloroform, at a temperature from about −10° C. to about 50° C., preferably from about 0° C. to about 30° C.

Scheme 1.

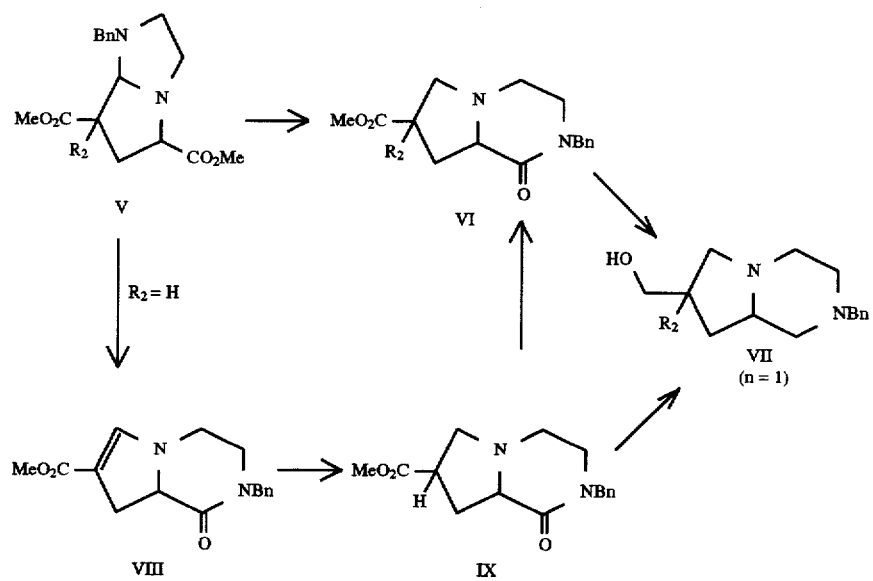

Scheme 2.

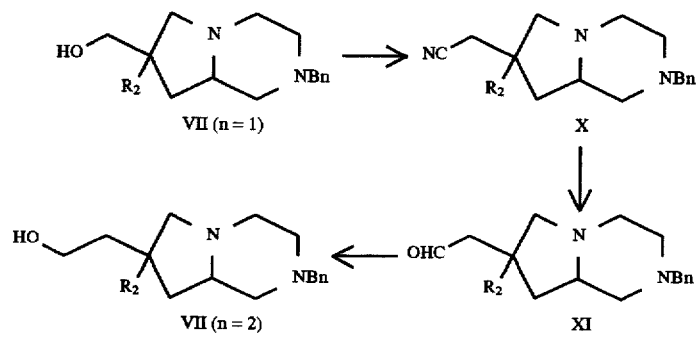

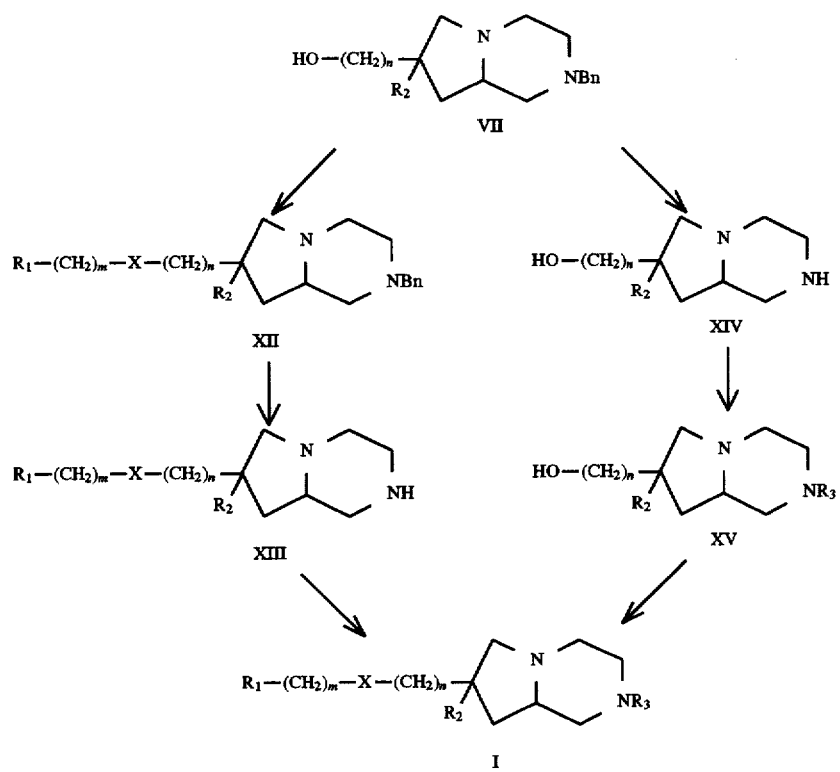
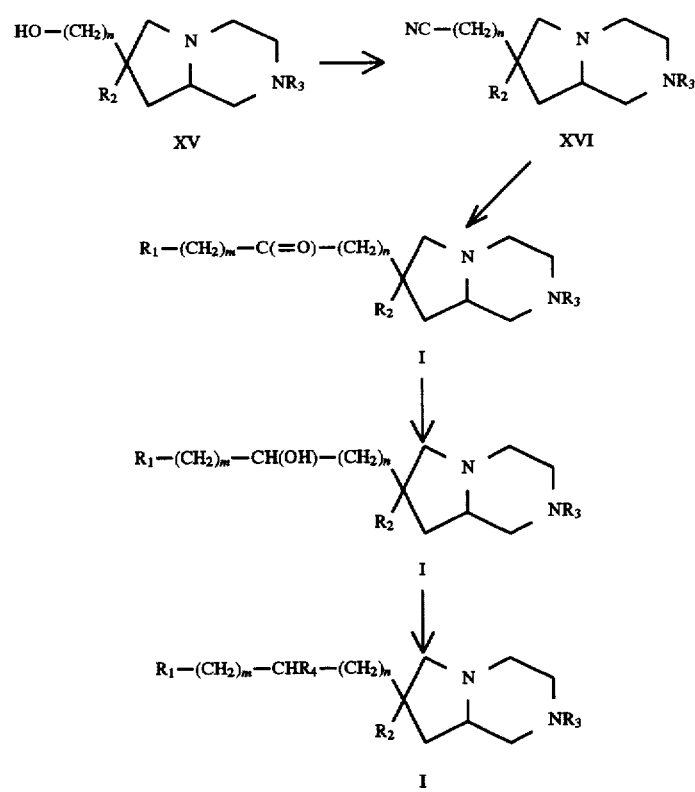

Scheme 5.

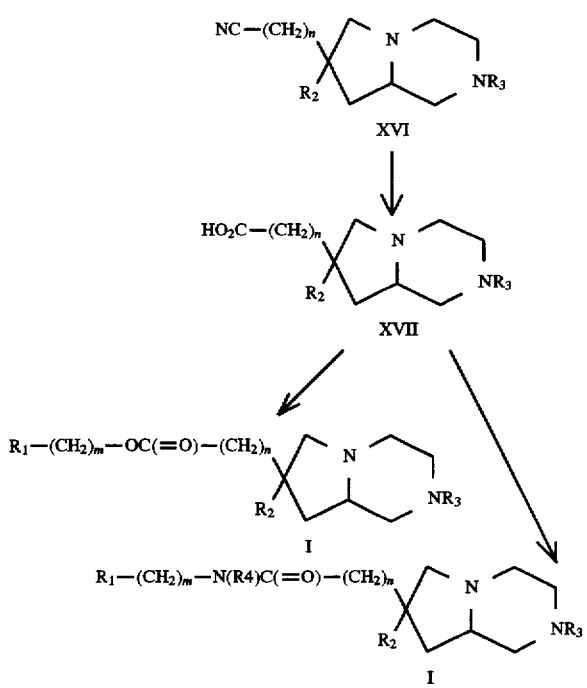

Scheme 6.

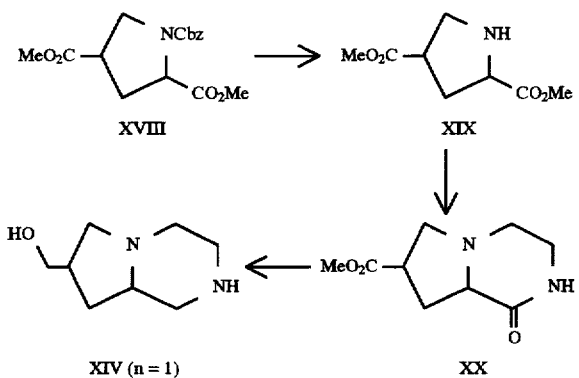

The novel compounds of the formula I and the pharmaceutically acceptable salts thereof (herein "the therapeutic compounds of this invention") are useful as dopaminergic agents, i.e., they possess the ability to alter dopamine mediated neurotransmission in mammals, including humans. They are therefore able to function as therapeutic agents in the treatment of a variety of conditions in mammals, the treatment or prevention of which can be effected or facilitated by an increase or decrease in dopamine mediated neurotransmission.

The compounds of the formula I that are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

The therapeutic compounds of this invention can be administered orally, transdermally (e.g. through the use of a patch), parenterally or topically. Oral administration is preferred. In general, these compounds are most desirably administered in dosages ranging from about 0.1 mg up to about 1000 mg per day, or 1 mg to 1000 mg per day in some cases, although variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds of the invention may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, for example. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

Dopaminergic activity is related to the ability of compounds to bind to mammalian dopamine receptors, and the relative ability of compounds of this invention to inhibit [$^3$H]-spiperone binding to human dopamine $D_4$ receptor subtypes expressed in clonal cell lines was measured using the following procedure.

The determination of $D_4$ receptor binding ability has been described by Van Tol, et al. (*Nature*, 1991, 350, 610). Clonal cell lines expressing the human dopamine $D_4$ receptor are harvested and homogenized (polytron) in a 50 mM Tris:HCl (pH 7.4 at 4° C.) buffer containing 5 mM EDTA, 1.5 mM calcium chloride (CaCl$_2$), 5 mM magnesium chloride (MgCl$_2$), 5 mM potassium chloride (KCl) and 120 mM sodium chloride (NaCl). The homogenates are centrifugated for 10–15 min. at 48,000 g, and the resulting pellets resuspended in a buffer at a concentration of 150–250 mg/ml. For saturation experiments, 0.75 ml aliquots of tissue homogenate are incubated in triplicate with increasing concentrations of [$^3$H]-spiperone (70.3 Ci/mmol; 10–3000 pM final concentration) for 30–120 minutes at 22° C. in a total volume of 1 ml. For competition binding experiments, assays are initiated by the addition of 0.75 ml of membrane and incubated in duplicate with the indicated concentrations of competing ligands ($10^{-14}$–$10^{-3}$M) and/or [$^3$H]-spiperone (100–300 pM) for 60–120 min at 22° C. Assays are terminated by rapid filtration through a Brandell cell harvester and the filters subsequently monitored for tritium as described by Sunahara, R. K. et al. (*Nature*, 1990, 346, 76). For all experiments, specific [$^3$H]spiperone binding is defined as that inhibited by 1–10 mM (+)-butaclamol. Binding data are analyzed by non-linear least square curve-fitting. The compounds of the Examples were tested in this assay, and all were found to have binding affinities ($K_i$) for the displacement of [$^3$H]-spiperone of less than 2 micromolar.

The following Examples are provided solely for the purposes of illustration and do not limit the invention which is defined by the claims.

EXAMPLE 1

(7RS,8aSR)-7-(4-Fluorophenoxy)methyl-2-(5-fluoropyrimidin-2-yl)-1,2,3,4,6,7,8,8a-octahydro-pyrrolo[1,2-a]pyrazine

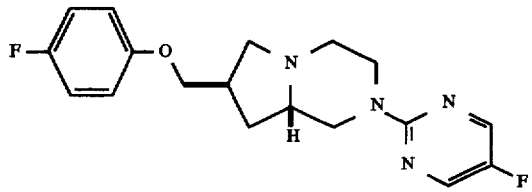

A solution of 2.00 g (5.9 mmol) of (7RS,8aSR)-7-(4-fluorophenoxy)methyl-2-phenylmethyl-1,2,3,4,6,7,8,8a-octahydro-pyrrolo[1,2-a]pyrazine (Preparation 2) and 4.1 mL (20.6 mmol) of 5M aqueous ammonium formate in 50 mL methanol was treated with an aqueous slurry of 0.200 g of 10% Pd/C. The reaction was refluxed for 48 hrs. The mixture was filtered and the solvent removed in vacuo to give an oily residue. The crude (7RS,8aSR)-7-(4-fluorophenoxy)methyl-1,2,3,4,6,7,8,8a-octahydro-pyrrolo [1,2-a]pyrazine was combined with 1.2 g (9.1 mmol) of 2-chloro-5-fluoropyrimidine (Dunaiskis, A.; et al. *Org. Prep. Proc. Int.*, 1995, 27, 600–602), 2.0 g (9.1 mmol) of sodium carbonate in 100 mL of water, and the mixture was gently refluxed for 16 hrs. After cooling to room temperature, the mixture was extracted with methylene chloride (3×). The combined organic layers were dried (magnesium sulfate), filtered, and evaporated. Purification by flash silica gel chromatography eluting with 90:10 ethyl acetate:hexane gave 0.744 g (27%) of the title compound. mp (.HCl) 120°–122° C. $^{13}$C NMR (base, CDCl$_3$): δ 31.4, 35.3, 43.8, 49.0, 51.5, 57.6, 61.5, 71.4, 115.39, 115.50, 115.62, 115.92, 144.96, 145.24, 149.9, 153.2, 155.1, 155.7, 158.8. Anal calcd for C$_{18}$H$_{20}$F$_2$N$_4$O: C, 62.41; H, 5.82; N, 16.18. Found: C, 62.05, H, 5.99; N, 16.33.

EXAMPLE 2

(7SR,8aSR)-7-(4-Fluorophenoxy)methyl-2-(5-fluoropyrimidin-2-yl)-1,2,3,4,6,7,8,8a-octahydro-pyrrolo[1,2-a]pyrazine

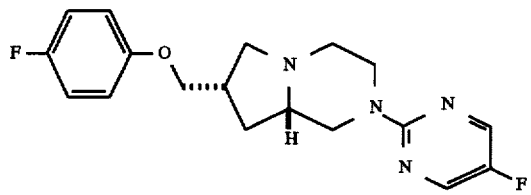

A solution of 0.870 g (2.6 mmol) of (7SR,8aSR)-7-(4-fluorophenoxy)methyl-2-phenylmethyl-1,2,3,4,6,7,8,8a-octahydro-pyrrolo[1,2-a]pyrazine (Preparation 2) and 1.8 mL (8.9 mmol) of 5M aqueous ammonium formate in 50 mL methanol was treated with an aqueous slurry of 0.100 g of 10% Pd/C. The reaction was refluxed for 24 h. The mixture was filtered and the solvent removed in vacuo to give an oily residue. The crude (7SR,8aSR)-7-(4-fluorophenoxy)methyl-1,2,3,4,6,7,8,8a-octahydro-pyrrolo[1,2-a]pyrazine was combined with 0.373 g (2.8 mmol) of 2-chloro-5-fluoropyrimidine (Dunaiskis, A.; et al. *Org. Prep. Proc. Int.*, 1995, 27, 600–602), 0.650 g (6.1 mmol) of sodium carbonate in 50 mL of water, and the mixture was gently refluxed for 16 hrs. After cooling to room temperature, the mixture was extracted with methylene chloride (3×). The combined organic layers were dried (magnesium sulfate), filtered, and evaporated. Purification by silica gel flash chromatography eluting with 85:15 ethyl acetate:hexane gave 0.444 g (50%) of the title compound. mp (.HCl) 211°–213° C. $^{13}$C NMR (base, CDCl$_3$): δ 31.7, 35.2, 43.8, 49.1, 51.4, 56.6, 62.3, 72.5, 115.45, 115.56, 115.89, 144.95, 145.24, 149.9, 153.2, 155.1, 155.6, 158.79, 158.90. Anal calcd for C$_{18}$H$_{20}$F$_2$N$_4$O: C, 62.41; H, 5.82; N, 16.18. Found: C, 62.15, H, 5.99; N, 16.38.

EXAMPLE 3

(7RS,8aSR)-7-(4-Fluorophenoxy)methyl-2-(5-fluoropyrimidin-2-yl)-7-methyl-1,2,3,4,6,7,8,8a-octahydro-pyrrolo[1,2-a]pyrazine

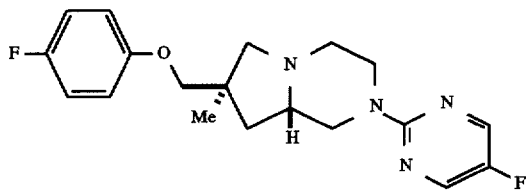

A solution of 0.745 g (2.80 mmol) of (7RS,8aSR)-7-hydroxymethyl-2-(5-fluoropyrimidin-2-yl)-7-methyl-1,2,3,4,6,7,8,8a-octahydro-pyrrolo[1,2-a]pyrazine (Preparation 5) and 0.43 mL (3.08 mmol) of triethylamine in 30 mL of dry methylene chloride was chilled to 0° C., and treated with methanesulfonyl chloride (0.228 mL, 2.94 mmol) in 15 mL of dry methylene chloride. After 1 h, the solution was washed with water (2×), dried (magnesium sulfate), filtered and evaporated to give 0.915 g (95%) of mesylate as a pale yellow solid.

A solution of 0.23 g (2.0 mmol) of 4-fluorophenol in 10 mL of dry DMF was treated with 0.096 g (2.4 mmol) of sodium hydride (60% oil dispersion), and the mixture heated at 50° C. for 1 h. A solution of 0.25 g (0.73 mmol) of mesylate in 10 mL of dry DMF was added and the solution heated at 100° C. for 72 h. The mixture was cooled to room temperature, diluted with water, and extracted with diethyl ether (2×). The organic phase was dried (magnesium sulfate), filtered and evaporated. Purification by flash silica gel chromatography eluting with 2:1 petroleum ether:diethyl ether gave 0.15 g (58%) of the title compound. mp (.HCl) 158°–160° C. $^{13}$C NMR (base, CDCl$_3$): δ 26.4, 39.9, 40.6, 43.8, 49.1, 51.6, 62.8, 64.5, 76.0, 115.3, 115.5, 115.6, 115.9, 145.0, 145.2, 149.9, 153.2, 155.4, 155.7, 158.8, 158.9. HRMS calcd for $C_{19}H_{23}F_2N_4O$ (MH+): 361.1840; found: 361.1861.

EXAMPLE 4

(7RS,8aSR)-7-Phenoxymethyl-2-(5-fluoropyrimidin-2-yl)-7-methyl-1,2,3,4,6,7,8,8a-octahydro-pyrrolo[1,2-a]pyrazine

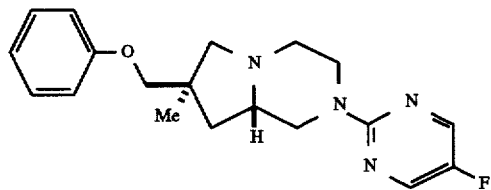

A solution of 0.745 g (2.80 mmol) of (7RS,8aSR)-7-hydroxymethyl-2-(5-fluoropyrimidin-2-yl)-7-methyl-1,2,3,4,6,7,8,8a-octahydro-pyrrolo[1,2-a]pyrazine (Preparation 5) and 0.43 mL (3.08 mmol) of triethylamine in 30 mL of dry methylene chloride was chilled to 0° C., and treated with methanesulfonyl chloride (0.228 mL, 2.94 mmol) in 15 mL of dry methylene chloride. After 1 h, the solution was washed with water (2×), dried (magnesium sulfate), filtered and evaporated to give 0.915 g (95%) of mesylate as a pale yellow solid.

A solution of 0.19 g (2.0 mmol) of phenol in 10 mL of dry DMF was treated with 0.096 g (2.4 mmol) of sodium hydride (60% oil dispersion), and the mixture heated at 50° C. for 1 h. A solution of 0.25 g (0.73 mmol) of mesylate in 10 mL of dry DMF was added and the solution heated at 100° C. for 72 h. The mixture was cooled to room temperature, diluted with water, and extracted with diethyl ether (2×). The organic phase was dried (magnesium sulfate), filtered and evaporated. Purification by flash silica gel chromatography eluting with petroleum ether:diethyl ether (2:1) gave 0.18 g (72%) of the title compound. mp (.HCl) 189°–191° C. $^{13}$C NMR (base, CDCl$_3$): δ 26.4, 40.0, 40.6, 43.8, 49.1, 51.6, 62.8, 64.5, 75.3, 114.5, 120.7, 129.4, 145.0, 145.2, 149.9, 153.2, 158.9, 159.3. HRMS calcd for $C_{19}H_{23}FN_4O$ (MH+): 343.1934; found: 343.1951.

EXAMPLE 5

(7RS,8aSR)-7-(4-Fluorophenoxy)methyl-2-(5-chloropyridin-2-yl)-1,2,3,4,6,7,8,8a-octahydro-pyrrolo[1,2-a]pyrazine

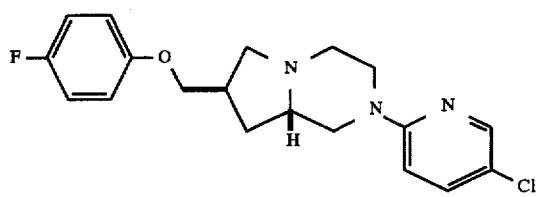

A mixture of 3.8 g (26 mmol) of 2,5-dichloropyridine, 1.3 g (12 mmol) of sodium carbonate, 1.3 g (5.2 mmol) of (7RS,8aSR)-7-(4-fluorophenoxy)methyl-1,2,3,4,6,7,8,8a-octahydro-pyrrolo[1,2-a]pyrazine (Preparation 2), and 20 mL of isoamyl alcohol was heated at reflux for 18 h. The solvent was evaporated, the residue taken up in water and ethyl acetate, and the pH adjusted to 11 with sodium carbonate. The layers were separated and the organic phase was dried (magnesium sulfate), filtered, and evaporated. Purification by medium pressure silica gel chromatography with ethyl acetate gave 35 mg (2%) of the title compound. mp (.HCl) 202°–206° C. HRMS calcd for $C_{19}H_{21}ClFN_3O$ (MH+): 362.1435, found: 362.1451.

EXAMPLE 6

(7S,8aS)-7-(4-Fluorophenoxy)-2-(5-fluoropyrimidin-2-yl)-1,2,3,4,6,7,8,8a-octahydro-pyrrolo[1,2-a]pyrazine

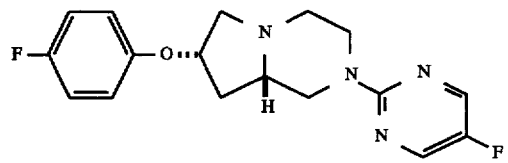

A solution of 0.971 g (4.18 mmol) of (7R,8aS)-7-hydroxy-2-phenylmethyl-1,2,3,4,6,7,8,8a-octahydro-pyrrolo[1,2-a]pyrazine (Diafi, L.; et al. *J. Het. Chem.*, 1990, 27, 2181), 0.703 g (6.27 mmol) of 4-fluorophenol and 1.32 g (5.02 mmol) of triphenylphosphine in 20 mL of dry THF was treated with 0.79 mL (5.02 mmol) of diethyl azodicarboxylate and the solution stirred at room temperature for 21 h. Excess HCl (g) in diethyl ether was added, the precipitate was collected on a Büchner funnel, washing with ethyl acetate. The gummy residue was dissolved in a mixture of ethyl acetate and aqueous ammonium hydroxide, the layers were separated, the aqueous phase was extracted with more ethyl acetate (2×), the combined organic phase was dried (magnesium sulfate), filtered and evaporated. Purification by silica gel MPLC with 95:5 ethyl acetate:methanol gave 1.3 g (95%) of (7S,8aS)-7-(4-fluorophenoxy)-2-phenylmethyl-1,2,3,4,6,7,8,8a-octahydro-pyrrolo[1,2-a]pyrazine.

A solution of 0.83 g (2.5 mmol) of (7S,8aS)-7-(4-fluorophenoxy)-2-phenylmethyl-1,2,3,4,6,7,8,8a-octahydro-pyrrolo[1,2-a]pyrazine in 10 mL of methanol and 1.8 mL of aqueous ammonium formate (5M) was treated with an aqueous slurry of 0.325 g of 10% palladium on carbon and the mixture was stirred at room temperature for 24 h. The mixture was filtered through Celite, evaporated, re-evaporated with another 100 mL of chloroform, dissolved in 100 mL of chloroform, dried (magnesium sulfate), filtered and evaporated. The crude amine (0.61 g, ca. 2.5 mmol), 0.50 g (3.75 mmol) of 2-chloro-5-fluoropyrimidine (Dunaiskis, A.; et al. Org. Prep. Proc. Int., 1995, 27, 600–602), 0.86 g (6.2 mmol) of potassium carbonate and 15 mL of 2-propanol were refluxed for 5.5 h. The mixture was cooled to room temperature, diluted with water, and extracted with ethyl acetate (3×). The combined organic phase was washed with water (2×) and brine (1×), dried (magnesium sulfate), filtered and evaporated. Purification by silica gel MPLC starting with 70:30 ethyl acetate:hexane and ramping to 50:50 ethyl acetate:hexane at 30 min, gave 0.30 g (36%) of the title compound. mp (.HCl) 90°–95 °C. $^{13}$C NMR (base, CDCl$_3$): δ 36.6, 43.6, 48.7, 60.5, 62.1, 75.6, 115.67, 115.98, 116.08, 116.18, 144.97, 145.26, 149.9, 153.2, 153.8, 155.6, 158.8. HRMS calcd for C$_{17}$H$_{19}$F$_2$N$_4$O (MH+): 333.1527, found: 333.1556.

EXAMPLE 7

(7R,8aS)-7-(4-Fluorobenzyl)oxy-2-(5-fluoropyrimidin-2-yl)-1,2,3,4,6,7,8,8a-octahydro-pyrrolo[1,2-a]pyrazine

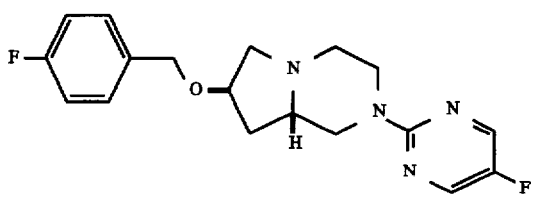

A solution of 0.75 g (3.15 mmol) of (7R,8aS)-7-hydroxy-2-(5-fluoropyrimidin-2-yl)-1,2,3,4,6,7,8,8a-octahydro-pyrrolo[1,2-a]pyrazine (Preparation 6) and 0.79 mL (6.3 mmol) of 4-fluorobenzyl bromide in 30 mL of dry DMF was treated with 0.15 g (3.8 mmol) of sodium hydride (60% oil dispersion), and the mixture was heated at 100° C. for 18 h. The mixture was cool, diluted with water, and extracted with diethyl ether (5×). The combined organic phase was dried (magnesium sulfate), filtered and evaporated. Purification by flash silica gel chromatograph with 50:50 ethyl acetate:hexane gave 0.090 g (8%) of the title compound. mp (.HCl) 74°–79° C. $^{13}$C NMR (base, CDCl$_3$): δ 35.6, 43.9, 48.9, 51.2, 60.4, 60.7, 70.7, 76.7, 115.1, 115.4, 129.35, 129.46, 133.9, 144.9, 145.2, 149.9, 153.2, 158.9, 164.0. HRMS calcd for C$_{18}$H$_{20}$F$_2$N$_4$O (MH+): 347.1683, found: 347.1671.

EXAMPLE 8

(7S,8aS)-7-(4-Fluorobenzyl)oxy-2-(5-fluoropyrimidin-2-yl)-1,2,3,4,6,7,8,8a-octahydro-pyrrolo[1,2-a]pyrazine

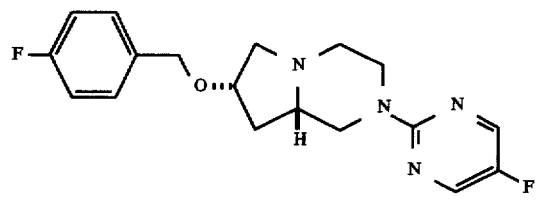

A solution of 1.15 mL (10.2 mmol) of 4-fluorobenzyl alcohol in 35 mL of dry DMF was treated with 0.48 g (12 mmol) of sodium hydride (60% oil dispersion), and the mixture was stirred at 50° C. for 30 min. A solution of 1.15 g (3.64 mmol) of (7R,8aS)-7-methanesulfonyloxy-2-(5-fluoropyrimidin-2-yl)-1,2,3,4,6,7,8,8a-octahydro-pyrrolo[1,2-a]pyrazine (Preparation 7) in 35 mL of dry DMF was added and the solution stirred at 100° C. for 18 h. The solution was cooled, diluted with water, and extracted with diethyl ether (2×). The combined organic phase was dried (magnesium sulfate), filtered and evaporated. Purification by flash silica gel chromatography with ethyl acetate gave 0.25 g (20%) of the title compound. mp (.D-(−)-tartrate) 76°–81° C. $^{13}$C NMR (base, CDCl$_3$): δ 36.3, 43.6, 48.8, 51.3, 60.2, 61.9, 70.4, 76.6, 115.0, 115.3, 129.43, 129.53, 134.0, 144.9, 145.2, 149.9, 153.2, 158.9, 160.6, 163.9. HRMS calcd for C$_{18}$H$_{20}$F$_2$N$_4$O (MH+): 347.1683, found: 347.1706.

EXAMPLE 9

(7S,8aS)-2-(5-Fluoropyrimidin-2-yl)-1,2,3,4,6,7,8,8a-octahydro-pyrrolo[1,2-a]pyrazin-7-yl benzoate

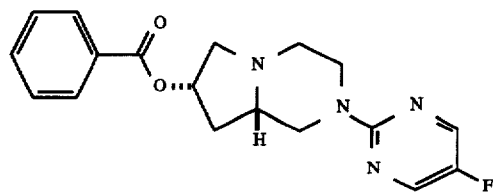

A solution of 2.0 g (8.4 mmol) of (7R,8aS)-7-hydroxy-2-(5-fluoropyrimidin-2-yl)-1,2,3,4,6,7,8,8a-octahydro-pyrrolo[1,2-a]pyrazine (Preparation 6), 1.54 g (12.6 mmol) of benzoic acid, 2.65 g (10.1 mmol) of triphenylphosphine, and 1.59 mL (10.1 mmol) of diethyl azodicarboxylate (DEAD) in 85 mL of THF was stirred at ambient temperature for 16 h. The solvent was evaporated, and flash silica gel chromatography with 1:1 hexane:ethyl acetate gave 2.5 g of partially purified material. A second chromatography with 10:1 methylene chloride:methanol gave 1.68 g (59%) of the title compound. mp (.HCl) 134°–135.5° C. $^{13}$C NMR (base, CDCl$_3$): δ 36.1, 43.7, 48.7, 51.2, 60.4, 61.8, 73.2, 128.3, 129.7, 130.1, 133.0, 145.0, 145.3, 150.0, 153.1, 158.9, 166.7. HRMS calcd for C$_{18}$H$_{20}$FN$_4$O (MH+): 343.1570, found: 343.1585.

EXAMPLE 10

(7S,8aS)-7-(4-Fluorophenoxy)methyl-2-(5-fluoropyrimidin-2-yl)-1,2,3,4,6,7,8,8a-octahydro-pyrrolo[1,2-a]pyrazine

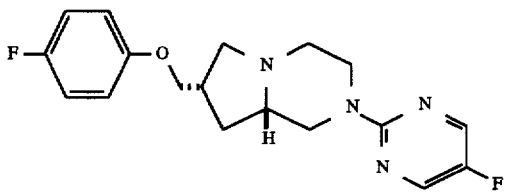

A solution of 0.25 g (0.99 mmol) of (7S,8aS)-7-hydroxymethyl-2-(5-fluoropyrimidin-2-yl)-1,2,3,4,6,7,8,8a-octahydro-pyrrolo[1,2-a]pyrazine (Preparation 13), 0.167 g (1.49 mmol) of 4-fluorophenol, 0.31 g (1.19 mmol) of triphenylphosphine and 0.19 mL (1.2 mmol) of diethyl azodicarboxylate (DEAD) in 10 mL of dry THF was stirred at ambient temperature for 16 h. The solvent was evaporated, the residue was dissolved in chloroform and washed with 1M sodium hydroxide. The organic phase was dried (magnesium sulfate), filtered and evaporated. Purification by flash silica gel chromatography with 1:1 hexane-:ethyl acetate and a second chromatography with 3:1 hexane:ethyl acetate gave 0.185 g (54%) of the title compound. mp (.HCl) 207.5°–208° C. $^{13}$C NMR (base, CDCl$_3$) δ 31.7, 35.2, 43.8, 49.1, 51.4, 56.6, 62.3, 72.5, 115.5, 115.6, 115.9, 144.9, 145.2, 149.9, 153.2, 155.1, 155.6, 158.8, 158.9. m/z (MH+) 347.

EXAMPLE 11

(7S,8aS)-7-(Substituted-phenoxy)methyl-2-(5-fluoropyrimidin-2-yl)-1,2,3,4,6,7,8,8a-octahydro-pyrrolo[1,2-a]pyrazines

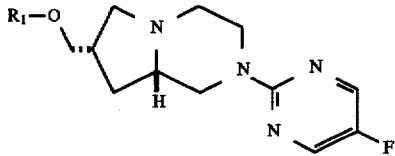

The following compounds were prepared from (7S,8aS)-7-hydroxymethyl-2-(5-fluoropyrimidin-2-yl)-1,2,3,4,6,7,8,8a-octahydro-pyrrolo[1,2-a]pyrazine (Preparation 13) and the appropriate phenol according to the method described in Example 10.

11a. (7S,8aS)-7-(3-Cyanophenoxy)methyl-2-(5-fluoropyrimidin-2-yl)-1,2,3,4,6,7,8,8a-octahydro-pyrrolo[1,2-a]pyrazine: mp (.HCl) 83°–85° C. HRMS calcd for C$_{19}$H$_{21}$FN$_5$O (MH+): 354.1730, found: 354.1716.

11b. (7S,8aS)-7-(4-Cyanophenoxy)methyl-2-(5-fluoropyrimidin-2-yl)-1,2,3,4,6,7,8,8a-octahydro-pyrrolo[1,2-a]pyrazine: mp (.HCl) 183°–185° C. HRMS calcd for C$_{19}$H$_{21}$FN$_5$O (MH+): 354.1730, found: 354.1719.

11c. (7S,8aS)-7-(3,5-Difluorophenoxy)methyl-2-(5-fluoropyrimidin-2-yl)-1,2,3,4,6,7,8,8a-octahydro-pyrrolo[1,2-a]pyrazine: mp (.HCl) 205°–206° C. HRMS calcd for C$_{18}$H$_{20}$F$_3$N$_4$O (MH+): 365.1589, found: 365.1592.

11d. (7S,8aS)-7-(2-Nitrophenoxy)methyl-2-(5-fluoropyrimidin-2-yl)-1,2,3,4,6,7,8,8a-octahydro-pyrrolo[1,2-a]pyrazine: mp (.HCl) 151°–153° C. HRMS calcd for C$_{18}$H$_{21}$FN$_5$O$_3$ (MH+): 374.1628, found: 374.1638.

11e. (7S,8aS)-7-(3-Nitrophenoxy)methyl-2-(5-fluoropyrimidin-2-yl)-1,2,3,4,6,7,8,8a-octahydro-pyrrolo[1,2-a]pyrazine: mp (.HCl) 92°–95° C. HRMS calcd for C$_{18}$H$_{21}$FN$_5$O$_3$ (MH+): 374.1628, found: 374.1647.

11f. (7S,8aS)-7-(4-Nitrophenoxy)methyl-2-(5-fluoropyrimidin-2-yl)-1,2,3,4,6,7,8,8a-octahydro-pyrrolo[1,2-a]pyrazine: mp (.HCl) 189°–191° C. HRMS calcd for C$_{18}$H$_{21}$FN$_5$O$_3$ (MH+): 374.1628, found: 374.1647.

11g. (7S,8aS)-7-(3-(Trifluoromethyl)phenoxy)methyl-2-(5-fluoropyrimidin-2-yl)-1,2,3,4,6,7,8,8a-octahydro-pyrrolo[1,2-a]pyrazine: HRMS calcd for C$_{19}$H$_{21}$F$_4$N$_4$O (MH+): 397.1651, found: 397.1642.

11h. (7S,8aS)-7-(4-(Cyanomethyl)phenoxy)methyl-2-(5-fluoropyrimidin-2-yl)-1,2,3,4,6,7,8,8a-octahydro-pyrrolo[1,2-a]pyrazine: mp (.HCl) 65°–67° C. HRMS calcd for C$_{20}$H$_{23}$FN$_5$O (MH+): 368.1887, found: 368.1898.

11i. (7S,8aS)-7-(4-((Methoxycarbonyl)methyl)phenoxy)methyl-2-(5-fluoropyrimidin-2-yl)-1,2,3,4,6,7,8,8a-octahydro-pyrrolo[1,2-a]pyrazine: mp (.HCl) 50°–52° C. HRMS calcd for C$_{21}$H$_{25}$FN$_4$O$_3$ (MH+): 401.1989, found: 401.1965.

11j. (7S,8aS)-7-(3-(Methoxycarbonyl)phenoxy)methyl-2-(5-fluoropyrimidin-2-yl)-1,2,3,4,6,7,8,8a-octahydro-pyrrolo[1,2-a]pyrazine: mp (.HCl) 74°–79° C. HRMS calcd for C$_{20}$H$_{24}$FN$_4$O$_3$ (MH+): 387.1832, found: 387.1866.

11k. (7S,8aS)-7-(3-(Ethynyl)phenoxy)methyl-2-(5-fluoropyrimidin-2-yl)-1,2,3,4,6,7,8,8a-octahydro-pyrrolo[1,2-a]pyrazine: mp (.HCl) 73°–76° C. HRMS calcd for C$_{20}$H$_{22}$FN$_4$O (MH+): 353.1778, found: 353.1805.

11l. (7S,8aS)-7-(3-(Ethoxy)phenoxy)methyl-2-(5-fluoropyrimidin-2-yl)-1,2,3,4,6,7,8,8a-octahydro-pyrrolo[1,2-a]pyrazine: mp (.HCl) 169°–170° C. HRMS calcd for C$_{20}$H$_{26}$FN$_4$O$_2$ (MH+): 373.2040, found: 373.2016.

11m. (7S,8aS)-7-(Phenoxy)methyl-2-(5-fluoropyrimidin-2-yl)-1,2,3,4,6,7,8,8a-octahydro-pyrrolo[1,2-a]pyrazine: mp (.HCl) 76°–79° C. HRMS calcd for C$_{18}$H$_{22}$FN$_4$O (MH+): 329.1778, found: 329.1784.

EXAMPLE 12

(7S,8aS)-7-(4-Fluorophenoxy)methyl-2-(5-chloropyridin-2-yl)-1,2,3,4,6,7,8,8a-octahydro-pyrrolo[1,2-a]pyrazine

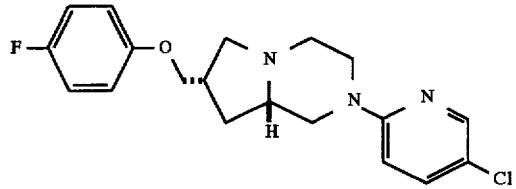

A solution of 0.25 g (0.93 mmol) of (7S,8aS)-7-hydroxymethyl-2-(5-chloropyridin-2-yl)-1,2,3,4,6,7,8,8a-octahydro-pyrrolo[1,2-a]pyrazine (Preparation 14), 0.157 g (1.40 mmol) of 4-fluorophenol, 0.29 g (1.12 mmol) of triphenylphosphine and 0.18 mL (1.1 mmol) of diethyl azodicarboxylate (DEAD) in 10 mL of dry THF was stirred at ambient temperature for 16 h. The solvent was evaporated, the residue was dissolved in chloroform and washed with 1M sodium hydroxide. The organic phase was dried (magnesium sulfate), filtered and evaporated. Purification by flash silica gel chromatography with 1:1 hexane-:ethyl acetate gave 0.24 g (71%) of the title compound. mp (.HCl) 221°–224° C. HRMS calcd for C$_{19}$H$_{22}$ClFN$_3$O (MH+): 362.1435, found: 362.1415.

EXAMPLE 13

(7S,8aS)-7-(Substituted-phenoxy)methyl-2-(5-chloropyridin-2-yl)-1,2,3,4,6,7,8,8a-octahydro-pyrrolo[1,2-a]pyrazines

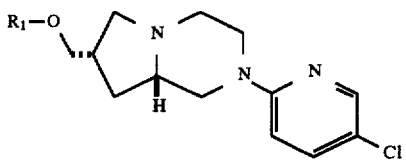

The following compounds were prepared from (7S,8aS)-7-hydroxymethyl-2-(5-chloropyridin-2-yl)-1,2,3,4,6,7,8,8a-octahydro-pyrrolo[1,2-a]pyrazine (Preparation 14) and the appropriate phenol according to the method described in Example 12.

13a. (7S,8aS)-7-(3-Cyanophenoxy)methyl-2-(5-chloropyridin-2-yl)-1,2,3,4,6,7,8,8a-octahydro-pyrrolo[1,2-a]pyrazine: mp (.HCl) 220°–224° C. HRMS calcd for $C_{20}H_{22}ClN_4O$ (MH+): 369.1482, found: 369.1472.

13b. (7S,8aS)-7-(4-Cyanophenoxy)methyl-2-(5-chloropyridin-2-yl)-1,2,3,4,6,7,8,8a-octahydro-pyrrolo[1,2-a]pyrazine. Purification by flash silica gel chromatography with ethyl ether. mp (.HCl) 245° C. (dec). HRMS calcd for $C_{20}H_{22}ClN_4O$ (MH+): 369.1482, found: 369.1465.

13c. (7S,8aS)-7-(3,5-Difluorophenoxy)methyl-2-(5-chloropyridin-2-yl)-1,2,3,4,6,7,8,8a-octahydro-pyrrolo[1,2-a]pyrazine. Purification by flash silica gel chromatography with 65:35 diethyl ether:petroleum ether. mp (.HCl) 220° C. (dec). HRMS calcd for $C_{19}H_{21}ClF_2N_3O$ (MH+): 380.1341, found: 380.1309.

13d (7S,8aS)-7-(4-(Methoxycarbonyl)methytphenoxy)methyl-2-(5-chloropyridin-2-yl)-1,2,3,4,6,7,8,8a-octahydro-pyrrolo[1,2-a]pyrazine: mp (.HCl) 186°–189° C. HRMS calcd for $C_{22}H_{27}ClN_3O_3$ (MH+): 416.1741, found: 416.1765.

EXAMPLE 14

(7S,8aS)-7-(3-Cyanophenoxy)methyl-2-(5-cyanopyridin-2-yl)-1,2,3,4,6,7,8,8a-octahydro-pyrrolo[1,2-a]pyrazine

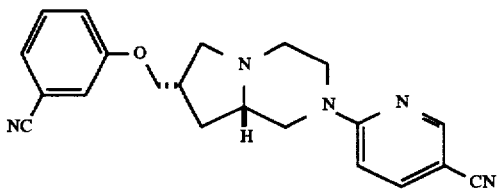

A solution of 1.0 g (6.4 mmol) of (7S,8aS)-7-hydroxymethyl-1,2,3,4,6,7,8,8a-octahydro-pyrrolo[1,2-a]pyrazine (Preparation 13, Step A), 1.77 g (12.8 mmol) of 2-chloro-5-cyanopyridine and 2.71 g (25.6 mmol) of sodium carbonate in 50 mL of isoamyl alcohol was heated at reflux for 18 h. The mixture was cooled to room temperature, diluted with ethyl acetate and water, the pH was adjusted to 11 with sodium carbonate, the layers were separated, and the aqueous layer extracted with ethyl acetate. The combined organic phase was dried (magnesium sulfate), filtered and evaporated to give (7S,8aS)-7-hydroxymethyl-2-(5-cyanopyridin-2-yl)-1,2,3,4,6,7,8,8a-octahydro-pyrrolo[1,2-a]pyrazine.

The (7S,8aS)-7-hydroxymethyl-2-(5-cyanopyridin-2-yl)-1,2,3,4 6,7,8,8a-octahydro-pyrrolo[1,2-a]pyrazine, 1.6 g (13.4 mmol) of 3-cyanophenol, and 2.8 g (11 mmol) of triphenylphosphine were dissolved in 20 mL of dry THF, the solution was treated with 1.7 mL (11 mmol) of diethyl azodicarboxylate (DEAD), and the reaction stirred at ambient temperature for 16 h. The solvent was evaporated, the residue taken up in ethyl acetate, and washed with 1M NaOH. The organic phase was extracted with 1M HCl (3×), and the aqueous acid was washed with ethyl acetate (1×). The aqueous phase was made basic with 1M NaOH, extracted with ethyl acetate (3×), and the combined organic phase dried (magnesium sulfate), filtered and evaporated. Purification by flash silica gel chromatography with 75:25 ethyl acetate:hexane gave 0.603 g (19%) of the title compound. mp (.HCl) 197°–200° C. HRMS calcd for $C_{21}H_{22}N_5O$ (MH+): 360.1824, found: 360.1802.

EXAMPLE 15

(7S,8aS)-7-(4-Fluorophenoxy)methyl-2-(5-cyanophenyl)-1,2,3,4,6,7,8,8 a-octahydro-pyrrolo[1,2-a]pyrazine

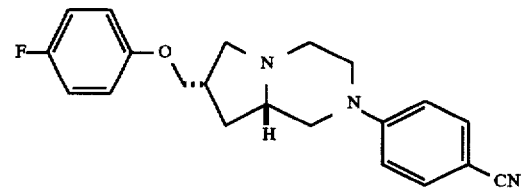

A solution of 0.25 g (0.97 mmol) of (7S,8aS)-7-hydroxymethyl-2-(4-cyanophenyl)-1,2,3,4,6,7,8,8a-octahydro-pyrrolo[1,2-a]pyrazine (Preparation 16), 0.164 g (1.46 mmol) of 4-fluorophenol, 0.31 g (1.15 mmol) of triphenylphosphine in 10 mL of THF was treated with 0.18 mL (1.15 mmol) of diethyl azodicarboxylate and the solution stirred at ambient temperature for 16 h. The solvent was removed by rotary evaporation, and the residue partitioned between chloroform and 1M sodium hydroxide. The layers were separated, and the organic phase was dried (magnesium sulfate), filtered and evaporated. Purification by flash silica gel chromatography with 1:1 ethyl acetate:hexane gave 0.225 g (66%) of the title compound. mp (.HCl) 81°–85° C. HRMS calcd for $C_{21}H_{23}FN_3O$ (MH+): 352.1825, found: 352.1817.

EXAMPLE 16

(7S,8aS)-7-(Substituted-phenoxy)methyl-2-(4-cyanophenyl)-1,2,3,4,6,7,8,8a-octahydro-pyrrolo[1,2-a]pyrazine

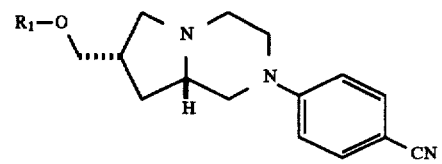

The following compounds were prepared from (7S,8aS)-7-hydroxymethyl-2-(4-cyanophenyl)-1,2,3,4,6,7,8,8a-octahydro-pyrrolo[1,2-a]pyrazine (Preparation 16) and the appropriate phenol according to the method described in Example 15.

16a. (7S,8aS)-7-(3-Cyanophenoxy)methyl-2-(4-cyanophenyl)-1,2,3,4,6,7,8,8a-octahydro-pyrrolo[1,2-a] pyrazine. mp 114°–118° C. HRMS calcd for $C_{22}H_{23}N_4O$ (MH+): 359.1872, found: 359.1877.

16b. (7S,8aS)-7-(4-Cyanophenoxy)methyl-2-(4-cyanophenyl)-1,2,3,4,6,7,8,8a-octahydro-pyrrolo[1,2-a] pyrazine. mp 128°–135° C. HRMS calcd for $C_{22}H_{23}N_4O$ (MH+): 359.1872, found: 359.1879.

16c. (7S,8aS)-7-(3-Ethoxyphenoxy)methyl-2-(4-cyanophenyl)-1,2,3,4,6,7,8,8a-octahydro-pyrrolo[1,2-a] pyrazine. mp 94°–98° C. HRMS calcd for $C_{23}H_{28}N_3O_2$ (MH+): 378.2182, found: 378.2145.

EXAMPLE 17

(7S,8aS)-2-(5-Chloropyridin-2-yl)-1,2,3,4,6,7,8,8a-octahydro-pyrrolo[1,2-a]pyrazin-7-yl benzoate

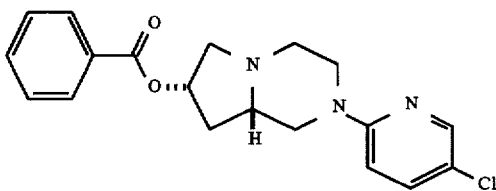

A solution of 0.595 g (2.35 mmol) of (7R,8aS)-7-hydroxy-2-(5-chloropyridin-2-yl)-1,2,3,4,6,7,8,8a-octahydro-pyrrolo[1,2-a]pyrazine (Preparation 17), 0.430 g (3.52 mmol) of benzoic acid and 0.738 g (2.81 mmol) of triphenylphosphine in 25 mL of dry THF was treated with 0.44 mL (2.8 mmol) of diethyl azodicarboxylate, and the mixture stirred at ambient temperature for 16 h. The solvent was evaporated and the residue purified by flash silica gel chromatography with 10:1 methylene chloride:acetone. A second chromatography of the major fraction with the same system gave 0.63 g (75%) of the title compound. mp (.HCl) 202°–205° C. HRMS calcd for $C_{19}H_{21}ClN_3O_2$ (MH+): 358.1322, found: 358.1320.

EXAMPLE 18

(7S,8aS)-7-(4-Fluorobenzyl)oxy-2-(5-chloropyridin-2-yl)-1,2,3,4,6,7,8,8a-octahydro-pyrrolo[1,2-a] pyrazine

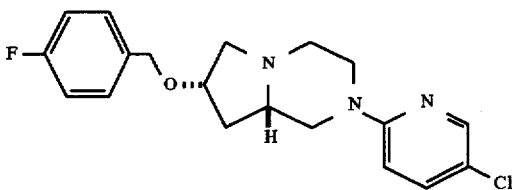

A solution of 0.23 g (0.91 mmol) of (7S,8aS)-7-hydroxy-2-(5-chloropyridin-2-yl)-1,2,3,4,6,7,8,8a-octahydro-pyrrolo[1,2-a]pyrazine (Preparation 18) in 10 mL of dry THF was treated with 40 mg (1.0 mmol) of sodium hydride (60% oil dispersion), followed by 0.125 mL (1.0 mmol) of 4-fluorobenzyl bromide and 17 mg (0.05 mmol) of tetra-n-butylammonium iodide. The mixture was stirred at ambient temperature for 16 h, and warmed to 50° C. for 4 h. The suspension was cooled, the solvent was evaporated, and the residue partitioned between ethyl acetate and water. The layers were separated, and the organic phase was dried (magnesium sulfate), filtered and evaporated. Purification by flash silica gel chromatography with 95:5 chloroform:methanol gave 0.135 g (41%) of the title compound. mp (.HCl) 165°–168° C. HRMS calcd for $C_{19}H_{22}ClFN_3O$ (MH+): 362.1435, found: 362.1451.

EXAMPLE 19

(7S,8aS)-7-(3-Cyanobenzyl)oxy-2-(5-fluoropyrimidin-2-yl)-1,2,3,4,6,7,8,8a-octahydro-pyrrolo[1,2-a]pyrazine

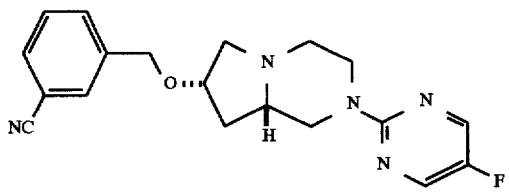

A solution of 0.60 g (2.5 mmol) of (7S,8aS)-7-hydroxy-2-(5-fluoropyrimidin-2-yl)-1,2,3,4,6,7,8,8a-octahydro-pyrrolo[1,2-a]-pyrazine (Preparation 15) in 30 mL of THF was treated with 0.41 g (10 mmol) of sodium hydride (60% oil dispersion), followed by 0.75 g (3.8 mmol) of 3-cyanobenzyl bromide and 30 mg (0.1 mmol) of tetra-n-butylammonium iodide. The mixture was stirred 50° C. for 16 h, cooled to room temperature, the solvent was evaporated, and the residue partitioned between ethyl acetate and water. The layers were separated, the organic phase was washed with water and brine, dried (magnesium sulfate), filtered and evaporated. Purification by MPLC silica gel chromatography with ethyl acetate gave 0.11 g (12%) of the title compound. mp (.HCl) 95°–100° C. HRMS calcd for $C_{19}H_{21}FN_5O$ (MH+): 345.1730; found: 345.1739.

EXAMPLE 20

(7S,8aS)-7-(4-(2-Hydroxyethyl)phenoxy)methyl-2-(5-fluoropyrimidin-2-yl)-1,2,3,4,6,7,8,8a-octahydro-pyrrolo[1,2-a]pyrazine

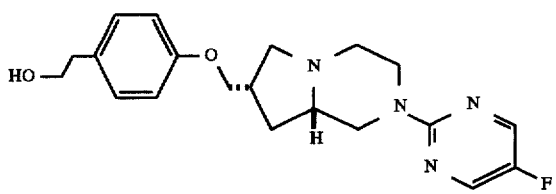

A solution of 0.13 g (0.33 mmol) of (7S,8aS)-7-(4-((methoxycarbonyl)methyl)phenoxy)methyl-2-(5-fluoropyrimidin-2-yl)-1,2,3,4,6,7,8,8a-octahydro-pyrrolo[1,2-a]pyrazine (Example 11i) in 15 mL of anhydrous ethyl ether was added dropwise to an ice-cold suspension of 0.025 g (0.65 mmol) of lithium aluminum hydride in 15 mL of anhydrous ethyl ether and the mixture stirred for 30 min. The reaction was carefully quenched at 0° C. with 0.025 mL of water, 0.025 mL of 15% sodium hydroxide, and 0.075 mL of water. The precipiate which formed was filtered through Celite, the filtrate concentrated in vacuo, and purification of the residue by flash silica gel chromatography with 95:5 ethyl acetate:methanol gave 0.075 g (63%) of the title compound. mp (.HCl) 145°–147° C. HRMS calcd for $C_{20}H_{26}FN_4O_2$ (MH+): 373.2040, found: 373.2054.

EXAMPLE 21

(7S,8aS)-7-(3-(Hydroxymethyl)phenoxy)methyl-2-(5-fluoropyrimidin-2-yl)-1,2,3,4,6,7,8,8a-octahydro-pyrrolo[1,2-a]pyrazine

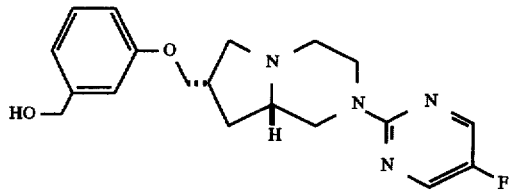

A solution of 0.15 g (0.39 mmol) of (7S,8aS)-7-(3-(methoxycarbonyl)phenoxy)methyl-2-(5-fluoropyrimidin-2-yl)-1,2,3,4,6,7,8,8a-octahydro-pyrrolo[1,2-a]pyrazine (Example 11j) in 15 mL of anhydrous ethyl ether was added dropwise to an ice-cold suspension of 0.029 g (0.78 mmol) of lithium aluminum hydride in 15 mL of anhydrous ethyl ether and the mixture stirred for 30 min. The reaction was carefully quenched at 0° C. with 0.029 mL of water, 0.029 mL of 15% sodium hydroxide, and 0.087 mL of water. The precipiate which formed was filtered through Celite, the filtrate concentrated in vacuo, and purification of the residue by flash silica gel chromatography with 95:5 chloroform:methanol gave 0.099 g (72%) of the title compound. mp (.HCl) 85°–89° C. HRMS calcd for $C_{19}H_{24}FN_4O_2$ (MH+): 359.1883, found: 359.1895.

EXAMPLE 22

(7S,8aS)-7-(4-(2-Hydroxyethyl)phenoxy)methyl-2-(5-chloropyridin-2-yl)-1,2,3,4,6,7,8,8a-octahydro-pyrrolo[1,2-a]pyrazine

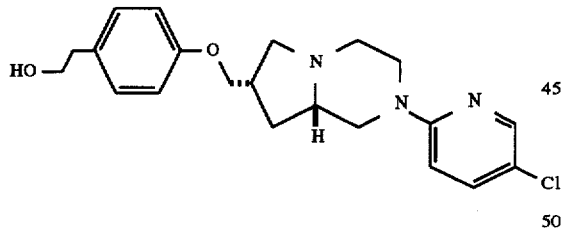

A solution of 0.15 g (0.33 mmol) of (7S,8aS)-7-(4-(methoxycarbonyl)methyl)phenoxy)methyl-2-(5-chloropyridin-2-yl)-1,2,3,4,6,7,8,8a-octahydro-pyrrolo[1,2-a]pyrazine (Example 13d) in 15 mL of anhydrous ethyl ether was added dropwise to an ice-cold suspension of 0.027 g (0.65 mmol) of lithium aluminum hydride in 15 mL of anhydrous ethyl ether and the mixture stirred for 30 min. The reaction was carefully quenched at 0° C. with 0.027 mL of water, 0.027 mL of 15% sodium hydroxide, and 0.081 mL of water. The precipiate which formed was filtered through Celite, the filtrate concentrated in vacuo, and purification of the residue by flash silica gel chromatography with 95:5 chloroform:methanol gave 0.13 g (95%) of the title compound. mp (.HCl) 199°–202° C. HRMS calcd for $C_{21}H_{27}ClN_3O_2$ (MH+): 388.1792, found: 388.1807.

EXAMPLE 23

(7S,8aS)-7-(4-Fluorophenoxy)methyl-2-(6-chloropyrazin-2-yl)-1,2,3,4,6,7,8,8a-octahydro-pyrrolo[1,2-a]pyrazine

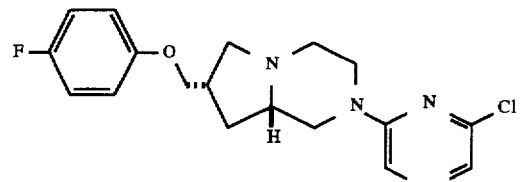

A mixture of 0.500 g (2.00 mmol) of (7SR,8aSR)-7-(4-fluoro-phenoxy)methyl-1,2,3,4,6,7,8,8a-octahydro-pyrrolo[1,2-a]pyrazine (Preparation 3), 1.49 g (10.0 mmol) of 2,6-dichloropyrazine, and 0.508 g (4.79 mmol) of sodium carbonate in 50 mL of isoamyl alcohol was heated to reflux for 16 h. The reaction was cooled to ambient temperature, the solvent removed in vacuo, the residue taken up in ethyl acetate and water, the pH was adjusted to 11 with sodium carbonate and the layers were separated. The aqueous phase was extracted with ethyl acetate, and the combined organic layers were dried (magnesium sulfate), filtered and evaporated. Purification by flash silica gel chromatography with 90:10 ethyl acetate:hexane gave 0.491 g (68%) of the title compound. mp (.HCl) 209°–212° C. HRMS calcd for $C_{18}H_{21}ClFN_4O$ (MH+): 363.1388, found: 363.1384.

EXAMPLE 24

(7S,8aS)-7-(4-Fluorophenoxy)methyl-2-(6-chloropyridazin-3-yl)-1,2,3,4,6,7,8,8a-octahydro-pyrrolo[1,2-a]pyrazine

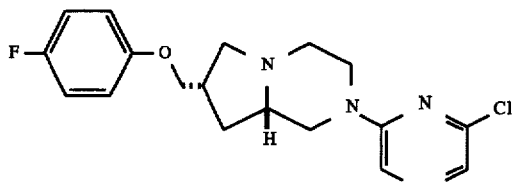

A mixture of 0.500 g (2.00 mmol) of (7SR,8aSR)-7-(4-fluoro-phenoxy)methyl-1,2,3,4,6,7,8,8a-octahydro-pyrrolo[1,2-a]pyrazine (Preparation 3), 1.49 g (10.0 mmol) of 3,6-dichloropyridazine, and 0.508 g (4.79 mmol) of sodium carbonate in 50 mL of isoamyl alcohol was heated to reflux for 48 h. The reaction was cooled to ambient temperature, the solvent removed in vacuo, the residue taken up in ethyl acetate and water, the pH was adjusted to 11 with sodium carbonate and the layers were separated. The aqueous phase was extracted with ethyl acetate, and the combined organic layers were dried (magnesium sulfate), filtered and evaporated. Purification by flash silica gel chromatography with 90:10 ethyl acetate:hexane gave 0.478 g (66%) of the title compound. mp (.HCl) 229° C. (dec). HRMS calcd for $C_{18}H_{21}ClFN_4O$ (MH+): 363.1388, found: 363.1404.

PREPARATION 1

7-Hydroxymethyl-2-phenylmethyl-1,2,3,4,6,7,8,8a-octahydro-pyrrolo[1,2-a]pyrazine

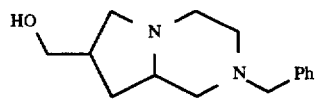

A suspension of 3.20 g (84.3 mmol) of lithium aluminum hydride in 30 mL of dry THF was cooled to 0° C. and treated dropwise with a solution of 8.00 g (27.7 mmol) of 7-methoxycarbonyl-2-phenylmethyl-1,2,3,4,6,7,8,8a-octahydro-pyrrolo[1,2-a]pyrazin-1-one (Jones, R. C. F.; Howard, K. J. *J. Chem. Soc., Perkin Trans. 1,* 1993, 2391) in 80 mL of dry THF. After 30 min the reaction was carefully quenched with 3 mL of water, 3 mL of 15% NaOH and 9 of mL water. The mixture was filtered, the filtrate evaporated, the residue taken up in ethyl acetate and washed with brine. The organic layer was dried (magnesium sulfate), filtered, and evaporated to give 6.09 g (89%) of the title compound as a mixture of (7RS,8aSR)- and (7SR,8aSR)- isomers of sufficient purity for use in the next reaction (Preparation 2). m/z (MH+) 247.

PREPARATION 2

(7RS,8aSR)- and (7SR,8aSR)-7-(4-Fluorophenoxy)methyl-2-phenylmethyl-1,2,3,4,6,7,8,8a-octahydro-pyrrolo[1,2-a]pyrazine

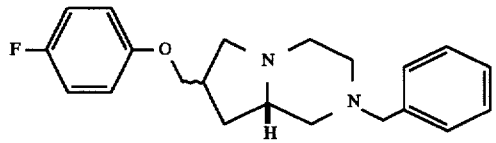

A solution of 6.00 g (24.35 mmol) of 7-hydroxymethyl-2-phenylmethyl-1,2,3,4,6,7,8,8a-octahydro-pyrrolo[1,2-a]pyrazine (Preparation 1), 4.10 g (36.5 mmol) of 4-fluorophenol and 7.70 g (29.4 mmol) of triphenylphosphine in 50 mL dry THF at 0° C. was treated dropwise with 4.6 mL (29.3 mmol) of diethyl azodicarboxylate. The reaction was allowed to warm to room temperature and stirred for 24 h. The solvent was evaporated, the residue taken up in ethyl acetate and washed with 1M NaOH (3×). The organic layer was dried (magnesium sulfate), filtered, and evaporated to give the crude product as a dark oil. Purification by flash silica gel chromatography eluting with 95:5 ethyl acetate:methanol gave 2.27 g (27%) of the (7RS,8aSR)- isomer and 0.410 g (5%) of the (7SR,8aSR)- isomer.

(7RS,8aSR)-7-(4-fluorophenoxy)methyl-2-phenylmethyl-1,2,3,4,6,7,8,8a-octahydro-pyrrolo[1,2-a]pyrazine: $^{13}C$ NMR (CDCl$_3$): δ 32.0, 35.5, 51.5, 52.5, 56.4, 57.7, 62.7, 62.9, 72.7, 115.45, 115.55, 115.86, 127.0, 128.2, 129.2, 138.3, 155.1, 155.6, 158.8.

(7SR,8aSR)-7-(4-fluorophenoxy)methyl-2-phenylmethyl-1,2,3,4,6,7,8,8a-octahydro-pyrrolo[1,2-a]pyrazine: $^{13}C$ NMR (CDCl$_3$): δ 31.6, 35.4, 51.6, 52.5, 57.4, 57.6, 61.7, 62.9, 71.6, 115.40, 115.51, 115.60, 115.91, 127.0, 128.2, 129.2, 138.2, 155.13, 155.15, 155.7, 158.8.

PREPARATION 3

(7SR,8aSR)-7-(4-Fluorophenoxy)methyl-1,2,3,4,6,7,8,8a-octahydro-pyrrolo[1,2-a]pyrazine

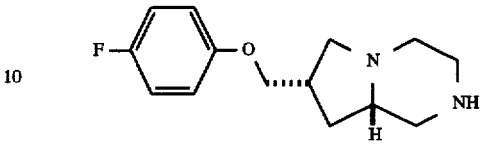

A mixture of 1.20 g (3.53 mmol) of (7SR,8aSR)-7-(4-fluorophenoxy)methyl-2-phenylmethyl-1,2,3,4,6,7,8,8a-octahydro-pyrrolo[1,2-a]pyrazine (Preparation 2), 30 mL of methanol and 2.5 mL of 5.0M ammonium formate was treated with an aqueous slurry of 0.15 g of 10% palladium on carbon. The mixture was heated at reflux for 48 h, cooled to ambient temperature, filtered through Celite, and the filtrate was evaporated. The residue was taken up in dilute aqueous ammonium hydroxide and extracted with chloroform (3×). The combined organic phase was dried (magnesium sulfate), filtered and evaporated to give 0.874 g (99%) of the title compound. $^{13}C$ NMR (CDCl$_3$): δ 32.0, 34.5, 45.2, 50.9, 53.4, 57.0, 63.7, 72.6, 115.4, 115.5, 115.8, 155.1, 155.6, 158.7. HRMS calcd for C$_{14}$H$_{20}$FN$_2$O (MH+): 251.156, found: 251.155.

PREPARATION 4

(7RS,8aSR)-7-Hydroxymethyl-7-methyl-2-phenylmethyl-1,2,3,4,6,7,8,8a-octahydro-pyrrolo[1,2-a]pyrazine

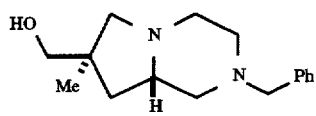

A solution of 3.33 g (11 mmol) of (7RS,8aSR)-7-methoxycarbonyl-7-methyl-2-phenylmethyl-1,2,3,4,6,7,8,8a-octahydro-pyrrolo[1,2-a]pyrazin-1-one (Jones, R. C. F.; Howard, K. J. *J. Chem. Soc., Perkin Trans. 1,* 1993, 2391) in 125 mL of dry THF was added dropwise to a stirred suspension of 1.26 g (33 mmol) of lithium aluminum hydride in 125 mL of dry THF. The solution was stirred for 2 h at room temperature, and carefully quenched with 1.26 mL of water, 1.26 mL of 15% NaOH, and 3.78 mL of water. After stirring for 30 min, the mixture was filtered through Celite, dried (magnesium sulfate), filtered and evaporated. Purification by flash silica gel chromatography eluting with 9:1 chloroform:methanol gave 1.67 g (58%) of the title compound. $^{13}C$ NMR (base, CDCl$_3$): δ 25.3, 39.7, 41.8, 51.1, 51.6, 57.1, 62.3, 62.9, 63.3, 71.3, 127.0, 128.2, 128.7, 129.2, 138.3. m/z (MH+) 261.

PREPARATION 5

(7RS,8aSR)-7-Hydroxymethyl-7-methyl-2-(5-fluoropyrimdin-2-yl)-1,2,3,4,6,7,8,8a-octahydro-pyrrolo[1,2-a]pyrazine

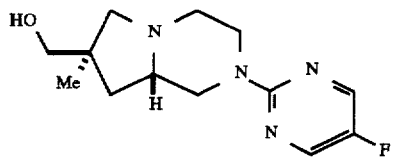

A solution of 1.65 g (6.35 mmol) of (7RS,8aSR)-7-hydroxymethyl-7-methyl-2-phenylmethyl-1,2,3,4,6,7,8,8a-octahydro-pyrrolo[1,2-a]pyrazine (Preparation 4) in 20 mL of methanol was mixed with 4.44 mL (22.2 mmol) of 5M aqueous ammonium formate, an aqueous slurry of 0.825 g of 10% palladium on carbon was added and the mixture was stirred at ambient temperature overnight. The solution was filtered through Celite and evaporated to give (7RS,8aSR)-7-hydroxymethyl-7-methyl-1,2,3,4,6,7,8,8a-octahydro-pyrrolo[1,2-a]pyrazine of sufficient purity for use in the next step.

A mixture of (7RS,8aSR)-7-hydroxymethyl-7-methyl-1,2,3,4,6,7,8,8a-octahydro-pyrrolo[1,2-a]pyrazine (1.08 g, 6.35 mmol), 0.925 g (6.98 mmol) of 2-chloro-5-fluoropyrimidine (Dunaiskis, A.; et al. *Org. Prep. Proc. Int.*, 1995, 27, 600–602), and 1.48 g (13.96 mmol) of sodium carbonate and 65 mL of water was heated at 90° C. for 72 h. the solution was cooled and extracted with chloroform (3×). The combined organic layers were dried (magnesium sulfate), filtered and evaporated. Purification by flash silica gel chromatography eluting with chloroform:methanol (95:5) gave 0.80 g (47%) of the title compound. $^{13}$C NMR (CDCl$_3$): a 25.5, 39.5, 41.7, 43.3, 48.7, 51.2, 62.3, 63.8, 71.0, 144.9, 145.2, 149.8, 153.1, 158.9. m/z (MH+) 267.

PREPARATION 6

(7R,8aS)-7-Hydroxy-2-(5-fluoropyrimidin-2-yl)-1,2,3,4,6,7,8,8a-octahydro-pyrrolo[1,2-a]pyrazine

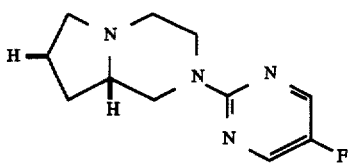

Step A

A solution of 9.75 g (42.0 mmol) of (7R,8aS)-7-hydroxy-2-phenylmethyl-1,2,3,4,6,7,8,8a-octahydro-pyrrolo[1,2-a]pyrazine (Diafi, L.; et al. *J. Het. Chem.*, 1990, 27, 2181) and 29.4 mL of 5M ammonium formate in 140 mL of methanol was treated with an aqueous slurry of 4.9 g of 10% palladium on carbon and the mixture was stirred at ambient temperature for 18 h. The mixture was filtered through Celite and evaporated to give (7R,8aS)-7-hydroxy-1,2,3,4,6,7,8,8a-octahydro-pyrrolo[1,2-a]pyrazine as a clear oil.

Step B

A mixture of the crude (7R,8aS)-7-hydroxy-1,2,3,4,6,7,8,8a-octahydro-pyrrolo[1,2-a]pyrazine, 9.96 g (52.5 mmol) of 2-chloro-5-fluoropyrimidine (Dunaiskis, A.; et al. *Org. Prep. Proc. Int.*, 1995, 27, 600–602), 13.4 g (126 mmol) of sodium carbonate and 450 mL of water was heated at 95° C. for 72 h. The mixture was cooled, extracted with chloroform (2×), and the combined organic phase was dried (magnesium sulfate), filtered and evaporated. Purification by flash silica gel chromatography with 95:5 ethyl acetate:methanol gave 8.54 g (85%) of the title compound. $^{13}$C NMR (base, CDCl$_3$): δ 39.1, 43.7, 48.7, 51.0, 60.2, 62.9, 69.4, 144.95, 145.24, 149.9, 153.2, 158.9. m/z (MH+) 239.

PREPARATION 7

(7R,8aS)-7-Methanesulfonyloxy-2-(5-fluoropyrimidin-2-yl)-1,2,3,4,6,7,8,8a-octahydro-pyrrolo[1,2-a]pyrazine

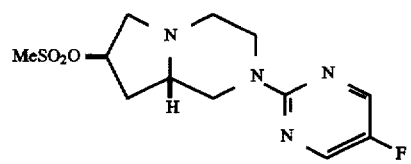

A solution of 1.00 g (4.20 mmol) of (7R,8aS)-7-hydroxy-2-(5-fluoropyrimidin-2-yl)-1,2,3,4,6,7,8,8a-octahydro-pyrrolo[1,2-a]-pyrazine (Preparation 6) and 0.644 mL (4.62 mmol) of triethylamine in 40 mL of methylene chloride was chilled to 0° C. and 0.34 mL (4.41 mmol) of methanesulfonyl chloride in 20 mL of methylene chloride was added slowly. After 30 min, water was added and the pH adjusted to 10 with 1M NaOH. The layers were separated, the organic phase was washed with water (2×), dried (magnesium sulfate), filtered and evaporated to give 1.15 g (86%) of the title compound of sufficient purity for use in subsequent reactions. m/z (MH+) 317.

PREPARATION 8

7-Methoxycarbonyl-2-phenylmethyl-1,2,3,4,8,8a-hexahydro-pyrrolo[1,2-a]pyrazin-1-one

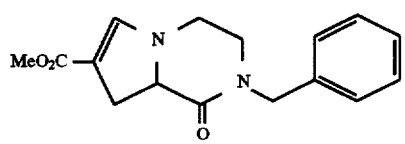

A solution of 8.6 g (27 mmol) of dimethyl 2-phenylmethyl-2,3,5,6,7,7a-hexahydro-1H-pyrrolo[1,2-c]imidazol-5,7-dioate (Jones, R. C. F.; Howard, K. J. *J. Chem. Soc. Perkin Trans.* 1, 1993, 2391) and 2.0 mL (13 mmol) of 1,8-diazabicyclo[5.4.0]undec-7-ene (DBU) in 150 mL of methanol was heated at reflux for 16 h. The solvent was evaporated, the residue was dissolved in ethyl acetate and washed with water (2×), dried (magnesium sulfate), filtered and evaporated to give 6.45 g (84%) of the title compound. $^{13}$C NMR (CDCl$_3$): δ 32.9, 43.9, 45.6, 50.5, 50.8, 63.1, 106.0, 127.7, 128.0, 128.8, 136.2, 148.1, 165.7, 170.0. HRMS calcd for $C_{16}H_{19}N_2O_3$ $_{(MH+)}$: 287.1396, found: 287.1406.

PREPARATION 9

(7SR,8aSR)-7-Methoxycarbonyl-2-phenylmethyl-1,2,3,4,6,7,8,8a-octahydro-pyrrolo[1,2-a]pyrazin-1-one

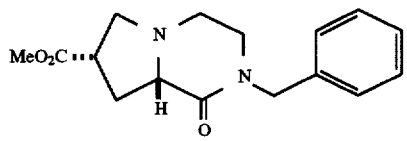

A mixture of 40.0 g (140 mmol) of 7-methoxycarbonyl-2-phenylmethyl-1,2,3,4,8,8a-hexahydro-pyrrolo[1,2-a]pyrazin-1-one (Preparation 8) and 10 g of 5% Pd on charcoal in 600 mL of ethyl acetate was shaken in a Parr apparatus under 50 psi of hydrogen gas for 6.5 h. The mixture was filtered through Celite, and the filtrate was evaporated to give 38.4 g (95%) of the title compound. $^{13}$C NMR (CDCl$_3$): δ 31.8, 41.4, 44.8, 46.5, 49.6, 52.1, 55.2, 64.0, 127.5, 128.1, 128.7, 128.8, 136.6, 169.6, 174.8. HRMS calcd for $C_{16}H_{22}N_2O_3$ (MH+): 289.1552, found: 289.1549.

PREPARATION 10

(7SR,8aSR)-7-Hydroxymethyl-2-phenylmethyl-1,2,3,4,6,7,8,8a-octahydro-pyrrolo[1,2-a]pyrazine

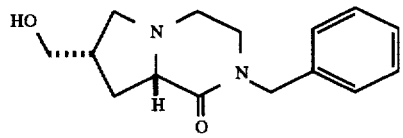

A three-neck flask fitted with a reflux condenser and dropping funnel was charged with 100 mL of dry THF and 2.4 g (63 mmol) of lithium aluminum hydride (LAH), and a solution of 6.0 g (21 mmol) of (7SR,8aSR)-7-methoxycarbonyl-2-phenylmethyl-1,2,3,4,6,7,8,8a-octahydro-pyrrolo[1,2-a]pyrazin-1-one (Preparation 9) in 60 mL of dry THF was placed in the dropping funnel. The LAH suspension was heated to reflux and the ester solution was added over a 30–60 min period. Reflux continued for another 4 h, the reaction was cooled in an ice bath and quenched by careful addition of 2.4 mL of water, 2.4 mL of 15% sodium hydroxide, and 7.2 mL of water. Stirring continued until a white precipitate formed, the mixture was filtered through Celite, and the filtrate was evaporated to give 5.0 g (97%) of the title compound of sufficient purity for use in subsequent reactions. $^{13}$C NMR (CDCl$_3$): δ 31.1, 37.2, 51.3, 52.6, 57.4, 62.8, 62.9, 67.4, 127.0, 128.2, 129.2, 138.2. HRMS calcd for $C_{15}H_{23}N_2O$ (MH+) 247.1810, found: 247.1800.

PREPARATION 11

(7S,8aS)-7-Methoxycarbonyl-1,2,3,4,6,7,8,8a-octahydro-pyrrolo[1,2-a]pyrazin-1-one

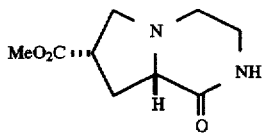

A mixture of 77.3 g (16 mmol) of N-benzyloxycarbonyl-cis-4-carboxy-L-proline dimethyl ester (Bridges, R. J; et al. *J. Med. Chem.*, 1991, 34, 717) and 169 mL (55 mmol) of 5M ammonium formate in 1000 mL of methanol was treated with an aqueous slurry of 15.5 g of 10% palladium on carbon. After 4 h, the mixture was filtered through Celite, the filtrate was concentrated to about 500 mL, saturated with sodium bicarbonate, and extracted with chloroform (5×). The aqueous layer was saturated with sodium chloride and extracted with chloroform (3×). The combined organic phase was dried (magnesium sulfate), filtered and evaporated to give 39.8 g (88%) of cis-4-carboxy-L-proline dimethyl ester.

A mixture of 39.8 g (213 mmol) of cis-4-carboxy-L-proline dimethyl ester, 40.2 g (213 mmol) of 2-(phthalimido) acetaldehyde (Preparation 12), and 17.5 g (213 mmol) of anhydrous sodium acetate in 2150 mL of dry methylene chloride was treated with 67.7 g (319 mmol) of sodium (triacetoxy)borohydride in small portions over a 1 h period. The solution was stirred for 16 h, water was added, and the pH adjusted to 10 with 1M sodium hydroxide. The organic phase was separated, dried (magnesium sulfate), filtered and evaporated to give 73.8 g (96%) of N-(2-(phthalimido)ethyl-cis-4-carboxy-L-proline dimethyl ester.

A solution of 73.8 g (205 mmol) of N-(2-(phthalimido) ethyl-cis-4-carboxy-L-proline dimethyl ester and 44.1 mL (513 mmol) of 40% aqueous methyl amine in 3100 mL of methanol was stirred at ambient temperature for 16 h. The solvent was evaporated and the crude product purified by flash silica gel chromatography starting with 4:1 diethyl ether:methanol and ending with 2:1 diethyl ether: methanol to give 37.0 g (91%) of the title compound of sufficient purity for use in subsequent reactions. m/z (MH+) 199.

Another sample of the title compound was purified further by flash silica gel chromatography with ethyl ether:methanol (9:1 to 8:2) and formed a white solid on standing. mp 70°–74° C. $^{13}$C NMR (d$_6$-DMSO): δ 32.2, 40.5, 42.4, 46.6, 52.6, 55.8, 64.0, 173.9, 176.2. HRMS calcd for $C_9H_{15}N_2O_3$ (MH+):199.1083, found: 199.1091.

PREPARATION 12

2-(Phthalimido)acetaldehyde

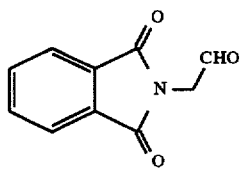

A solution of 50.0 g (190 mmol) of 2-(phthalimido) acetaldehyde diethyl acetal in 300 mL of toluene was treated with 150 mL of 50% aqueous trifluoroacetic acid and the mixture was stirred vigorously at ambient temperature for 72 h. The solution was concentrated in vacuo and 100 mL of ethyl acetate was added. The white precipitate was filtered off and washed with ice-cold ethyl acetate (100 mL) to give 30.0 g (78%) of the title compound.

PREPARATION 13

(7S,8aS)-7-Hydroxymethyl-2-(5-fluoropyrimidin-2-yl)-1,2,3,4,6,7,8,8a-octahydro-pyrrolo[1,2-a]pyrazine

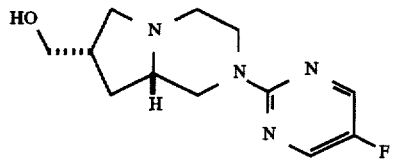

Step A

A solution of 1.75 g (8.84 mmol) of (7S,8aS)-7-methoxycarbonyl-1,2,3,4,6,7,8,8 a-octahydro-pyrrolo[1,2-a]pyrazin-1-one (Preparation 11) in 100 mL of THF was added dropwise to a suspension of 0.67 g (18 mmol) of lithium aluminum hydride in 100 mL of refluxing THF. After stirring for 1 h, the solution was cooled and carefully quenched with 0.67 mL of water, 0.67 mL of 15% sodium hydroxide, and 2.0 mL of water. The precipitate was filtered and the filtrate was concentrated to give 1.4 g of (7S,8aS)-7-hydroxymethyl-1,2,3,4,6,7,8,8a-octahydro-pyrrolo[1,2-a]pyrazine of sufficient purity for use in subsequent reactions.

Step B

A mixture of 1.38 g (8.84 mmol) of (7S,8aS)-7-hydroxymethyl-1,2,3,4,6,7,8,8a-octahydro-pyrrolo[1,2-a]pyrazine, 1.30 g (9.87 mmol) of 2-chloro-5-fluoropyrimidine (Dunaiskis, A.; et al. *Org. Prep. Proc. Int.*, 1995, 27, 600–602), and 2.85 g (26.9 mmol) of sodium carbonate and 90 mL of water was heated at 95° C. for 16 h. The solution was cooled and extracted with chloroform (2×), the combined organic phase was dried (magnesium sulfate), filtered and evaporated. Purification by flash silica gel chromatography with 9:1 chloroform:methanol gave 0.97 g (43%) of the title compound. mp 123°–124° C. m/z (MH+) 253. $^{13}$C NMR (CDCl$_3$): δ 30.9, 37.1, 43.8, 48.8, 51.3, 57.5, 62.6, 67.2, 144.9, 145.2, 149.9, 153.2, 158.8.

PREPARATION 14

(7S,8aS)-7-Hydroxymethyl-2-(5-chloropyridin-2-yl)-1,2,3,4,6,7,8,8a-octahydro-pyrrolo[1,2-a]pyrazine

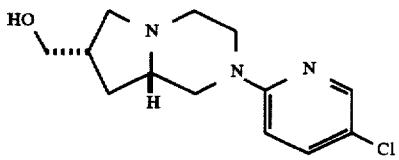

A mixture of 0.50 g (3.2 mmol) of (7S,8aS)-7-hydroxymethyl-1,2,3,4,6,7,8,8a-octahydro-pyrrolo[1,2-a]pyrazine (Preparation 13, Step A), 2.37 g (16.0 mmol) of 2,5-dichloropyridine, 0.85 g (8.0 mmol) of sodium carbonate and 35 mL of isoamyl alcohol was refluxed for 48 h. The hot solution was filtered and the filtrate evaporated. Purification by flash silica gel chromatography with 9:1 chloroform:methanol gave 0.25 g (29%) of the title compound. $^{13}$C NMR (CDCl$_3$): δ 31.1, 37.3, 44.7, 49.7, 51.2, 57.2, 62.5, 66.9, 107.9, 119.9, 137.1, 146.1, 157.6. m/z (MH+) 268.

PREPARATION 15

(7S,8aS)-7-Hydroxy-2-(5-fluoropyrimidin-2-yl)-1,2,3,4,6,7,8,8a-octahydro-pyrrolo[1,2-a]pyrazine

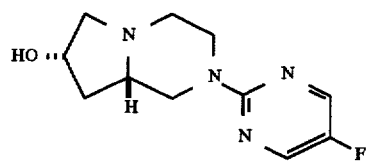

A solution of 1.58 g (4.61 mmol) of (7S,8aS)-2-(5-fluoropyrimidin-2-yl)-1,2,3,4,6,7,8,8a-octahydro-pyrrolo[1,2-a]pyrazin-7-yl benzoate (Example 9) in 200 mL of methanol was treated with 50 mL of 15% aqueous sodium hydroxide. After 30 min, the solvent was removed and the residue partitioned between water and ethyl acetate. The layers were separated, the organic phase was dried (magnesium sulfate), filtered and evaporated to give 0.922 g (84%) of the title compound. $^{13}$C NMR (CDCl$_3$): δ 39.4, 43.7, 49.0, 51.2, 62.2, 63.6, 69.9, 144.9, 145.2, 149.9, 153.2, 158.9. m/z (MH+) 239.

PREPARATION 16

(7S,8aS)-7-Hydroxymethyl-2-(4-cyanophenyl)-1,2,3,4,6,7,8,8a-octahydro-pyrrolo[1,2-a]pyrazine

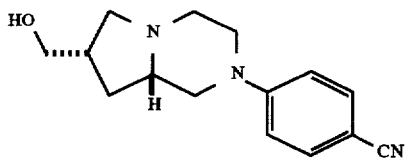

A mixture of 1.5 g (9.6 mmol) of (7S,8aS)-7-hydroxymethyl-1,2,3,4,6,7,8,8a-octahydro-pyrrolo[1,2-a]pyrazine (Preparation 13, Step A), 1.75 g (14.4 mmol) of 4-fluorobenzonitrile and 2.04 g (19.2 mmol) of sodium carbonate in 10 mL of DMSO was heated at 80° C. for 16 h. The solution was cooled to room temperature, diluted with water and extracted with 1:1 ethyl acetate:diethyl ether (3×). The combined organic phase was dried (magnesium sulfate), filtered and evaporated. Purification by flash silica gel chromatography with 9:1 chloroform: methanol gave 0.925 g (37%) of the title compound. $^{13}$C NMR (CDCl$_3$): δ 31.1, 37.2, 46.7, 51.0, 51.8, 57.6, 62.3, 67.3, 100.1, 114.3, 120.0, 133.5, 153.4. m/z (MH+) 258.

PREPARATION 17

(7R,8aS)-7-Hydroxy-2-(5-chloropyridin-2-yl)-1,2,3,4,6,7,8,8a-octahydro-pyrrolo[1,2-a]pyrazine

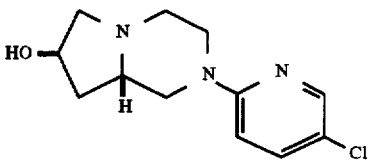

A mixture of 3.81 g (26.8 mmol) of (7R,8aS)-7-hydroxy-1,2,3,4,6,7,8,8a-octahydro-pyrrolo[1,2-a]pyrazine (Preparation 6, Step A), 19.8 g (134 mmol) of 2,5-dichloropyridine, 7.10 g (67.0 mmol) of sodium carbonate and 275 mL of isoamyl alcohol was heated at reflux for 72 h. The mixture was cooled to about 100° C., filtered hot, and the filtrate concentrated in vacuo. Purification of the residue by flash silica gel chromatography with 9:1 chloroform:methanol gave 0.63 g (9%) of the title compound of sufficient purity for use in subsequent reactions. m/z (MH+) 254.

PREPARATION 18

(7S,8aS)-7-Hydroxy-2-(5-chloropyridin-2-yl)-1,2,3,4,6,7,8,8a-octahydro-pyrrolo[1,2-a]pyrazine

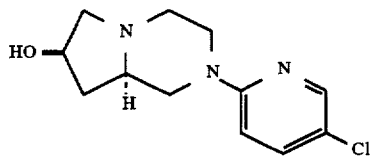

A solution of 0.52 g (1.45 mmol) of (7S,8aS)-2-(5-chloropyridin-2-yl)-1,2,3,4,6,7,8,8a-octahydro-pyrrolo[1,2-a]pyrazin-7-yl benzoate (Example 17) in 50 mL of methanol was treated with 50 mL of 15% aqueous sodium hydroxide and stirred at ambient temperature for 30 min. The solvent was concentrated by half in vacuo and the residue extracted with chloroform (3×). The combined organic phase was dried (magnesium sulfate), filtered and evaporated. Purification by flash silica gel chromatography with 9:1 chloroform:methanol gave 0.25 g (68%) of the title compound. mp (base) 167°–168° C. m/z (MH+) 254.

I claim:
1. A compound of formula I

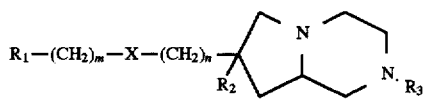

wherein $R_1$ is phenyl, naphthyl, benzoxazolonyl, indolyl, indolonyl, benzimidazolyl, quinolyl, furyl, benzofuryl, thienyl, benzothienyl, oxazolyl, benzoxazolyl;

$R_2$ is H or $(C_1-C_6)$alkyl;

$R_3$ is phenyl, pyridinyl, pyrimidinyl, pyrazinyl, or pyridazinyl;

$R_4$ is H or $(C_1-C_6)$alkyl;

$R_5$ is H or $(C_1-C_6)$alkyl;

wherein each group of $R_1$ and $R_3$ may be independently and optionally substituted with one to four substituents independently selected from the groups consisting of fluoro, chloro, bromo, iodo, cyano, nitro, thiocyano, —$SR_4$, —$SOR_4$, —$SO_2R_4$, —$NHSO_2R_4$, —$(C_1-C_6)$alkoxy, —$NR_4R_5$, —$NR_4COR_5$, —$CONR_4R_5$, phenyl, —$COR_4$, —$COOR_4$, —$(C_1-C_6)$alkyl, —$(C_1-C_6)$alkyl substituted with one to six halogens, —$(C_3-C_6)$cycloalkyl, and trifluoromethoxy;

X is O, S, SO, $SO_2$, $NR_4$, C=O, CH(OH), $CHR_4$,

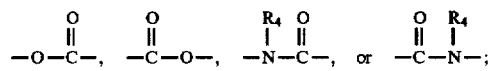

m is 0, 1 or 2;
n is 0, 1 or 2;
all stereoisomers thereof; or a pharmaceutically acceptable salt thereof.

2. A compound of claim 1 wherein $R_1$ is phenyl, naphthyl, benzoxazolonyl, indolyl, indolonyl, benzimidazolyl, or quinolyl;

wherein $R_1$ and $R_3$ may be independently substituted with up to three substituents independently selected from the group consisting of fluoro, chloro, bromo, iodo, cyano, —$NR_4R_5$, —$(C_1-C_6)$alkoxy, —$COOR_4$, —$CONR_4R_5$, —$(C_1C_6)$alkyl, —$(C_1-C_6)$alkyl substituted with one to six halogens, —$(C_3-C_6)$cycloalkyl, and trifluoromethoxy;

$R_2$ is H or $CH_3$;

X is O, C=O, CHOH, —C(=O)O—, or $CH_2$;

m is 0 or 1;

n is 0 or 1; or a pharmaceutically acceptable salt thereof.

3. A compound of claim 2 wherein $R_1$ is phenyl or substituted phenyl;

$R_3$ is substituted or unsubstituted phenyl, pyridinyl, or pyrimidinyl;

X is O, —C(=O)O—, or $CH_2$; or a pharmaceutically acceptable salt thereof.

4. A compound of claim 3 wherein $R_2$ is H;

X is O;

m is 0;

n is 1; or a pharmaceutically acceptable salt thereof.

5. A compound of claim 3 wherein $R_2$ is H;

X is O;

m is 1;

n is 0; or a pharmaceutically acceptable salt thereof.

6. A compound of claim 3 wherein $R_2$ is H;

X is —C(=O)O—;

m is 0;

n is 0; or a pharmaceutically acceptable salt thereof.

7. A compound of claim 4 wherein $R_1$ is fluorophenyl, diflurophenyl, or cyanophenyl;

$R_3$ is chloropyridinyl; or a pharmaceutically acceptable salt thereof.

8. A compound of claim 4 wherein $R_1$ is fluorophenyl, diflurophenyl, or cyanophenyl;

$R_3$ is fluoropyrimidinyl; or a pharmaceutically acceptable salt thereof.

9. A compound of claim 5 wherein $R_1$ is fluorophenyl, diflurophenyl, or cyanophenyl;

$R_3$ is chloropyridinyl; or a pharmaceutically acceptable salt thereof.

10. A compound of claim 5 wherein $R_1$ is fluorophenyl, diflurophenyl, or cyanophenyl;

$R_3$ is fluoropyrimidinyl; or a pharmaceutically acceptable salt thereof.

11. A compound of claim 6 wherein $R_1$ is fluorophenyl, diflurophenyl, or cyanophenyl;

$R_3$ is chloropyridinyl; or a pharmaceutically acceptable salt thereof.

12. A compound of claim 6 wherein
   $R_1$ is fluorophenyl, diflurophenyl, or cyanophenyl;
   $R_3$ is fluoropyrimidinyl; or
a pharmaceutically acceptable salt thereof.

13. A compound of claim 7 wherein
   $R_3$ is 5-chloro-pyridin-2-yl-; or
a pharmaceutically acceptable salt thereof.

14. A compound of claim 8 wherein
   $R_3$ is 5-fluoro-pyrimidin-2-yl-; or
a pharmaceutically acceptable salt thereof.

15. A compound of claim 9 wherein
   $R_3$ is 5-chloro-pyridin-2-yl-; or
a pharmaceutically acceptable salt thereof.

16. A compound of claim 10 wherein
   $R_3$ is 5-fluoro-pyrimidin-2-yl-; or
a pharmaceutically acceptable salt thereof.

17. A compound of claim 11 wherein
   $R_3$ is 5-chloro-pyridin-2-yl-; or
a pharmaceutically acceptable salt thereof.

18. A compound of claim 12 wherein
   $R_3$ is 5-fluoro-pyrimidin-2-yl-; or
a pharmaceutically acceptable salt thereof.

19. A compound of claim 1 which is (7S,8aS)-7-(4-fluorophenoxy)-methyl-2-(5-chloropyridin-2-yl)-1,2,3,4,6,7,8,8a-octahydro-pyrrolo[1,2-a]pyrazine.

20. A compound of claim 1 which is (7S,8aS)-7-(3,5-difluoro-phenoxy)methyl-2-(5-chloropyridin-2-yl)-1,2,3,4,6,7,8,8a-octahydro-pyrrolo[1,2-a]pyrazine.

21. A compound of claim 1 which is (7S,8aS)-7-(3-cyanophenoxy)methyl-2-(5-chloropyidin-2-yl)-1,2,3,4,6,7,8,8a-octahydro-pyrrolo[1,2-a]pyrazine.

22. A compound of claim 1 which is (7S,8aS)-7-(4-cyanophenoxy)methyl-2-(5-chloropyidin-2-yl)-1,2,3,4,6,7,8,8a-octahydro-pyrrolo[1,2- a]pyrazine.

23. A compound of claim 1 which is (7S,8aS)-7-(4-fluorobenzyl)oxy-2-(5-chloropyridin-2-yl)-1,2,3,4,6,7,8,8a-octahydro-pyrrolo[1,2-a]pyrazine.

24. A compound of claim 1 which is (7S,8aS)-2-(5-chloropyridin-2-yl)-1,2,3,4,6,7,8,8a-octahydro-pyrrolo[1,2-a]pyrazin-7-yl benzoate.

25. A compound of claim 1 which is (7S,8aS)-7-(4-fluorophenoxy)-methyl-2-(5-fluoropyrimidin-2-yl)-1,2,3,4,6,7,8,8a-octahydro-pyrrolo[1,2-a]pyrazine.

26. A compound of claim 1 which is (7S,8aS)-7-(3,5-difluorophenoxy)methyl-2-(5-fluoropyrimidin-2-yl)-1,2,3,4,6,7,8,8a-octahydro-pyrrolo[1,2-a]pyrazine.

27. A compound of claim 1 which is (7S,8aS)-7-(3-cyanophenoxy)-methyl-2-(5-fluoropyrimidin-2-yl)-1,2,3,4,6,7,8,8a-octahydro-pyrrolo[1,2-a]pyrazine.

28. A compound of claim 1 which is (7S,8aS)-7-(4-cyanophenoxy)-methyl-2-(5-fluoropyrimidin-2-yl)-1,2,3,4,6,7,8,8a-octahydro-pyrrolo[1,2-a]pyrazine.

29. A compound of claim 1 which is (7S,8aS)-7-(4-fluorobenzyl)oxy-2-(5-fluoropyrimidin-2-yl)-1,2,3,4,6,7,8,8a-octahydro-pyrrolo[1,2-a]pyrazine.

30. A compound of claim 1 which is (7S,8aS)-2-(5-fluoropyrimidin-2-yl)-1,2,3,4,6,7,8,8a-octahydro-pyrrolo[1,2-a]pyrazin-7-yl benzoate.

31. A compound of claim 1 which is (7S,8aS)-7-(3-cyanobenzyl)oxy-2-(5-fluoropyrimidin-2-yl)-1,2,3,4,6,7,8,8a-octahydro-pyrrolo[1,2-a]pyrazine.

32. A method for treating or preventing disorders of the dopamine system in a mammal, comprising administering to said mammal an amount of a compound according to claim 1, or a pharmaceutically acceptable salt thereof, that is effective in treating or preventing such disorder.

33. A method for treating or preventing psychotic disorders such as affective psychosis, schizophrenia, and schizoaffective disorders in a mammal, comprising administering to said mammal an amount of a compound according to claim 1, or a pharmaceutically acceptable salt thereof, that is effective in treating or preventing such disorder.

34. A method for treating or preventing movement disorders such as extrapyramidal side effects from neuroleptic agents, neuroleptic malignant syndrome, tardive dyskinesia, or Gilles De La Tourette's syndrome in a mammal, comprising administering to said mammal an amount of a compound according to claim 1, or a pharmaceutically acceptable salt thereof, that is effective in treating or preventing such disorder.

35. A method for treating or preventing movement disorders such as Parkinson's disease or Huntington's disease in a mammal, comprising administering to said mammal an amount of a compound according to claim 1, or a pharmaceutically acceptable salt thereof, that is effective in treating or preventing such disorder.

36. A method for treating or preventing gastrointestinal disorders such as gastric acid secretion in a mammal, comprising administering to said mammal an amount of a compound according to claim 1, or a pharmaceutically acceptable salt thereof, that is effective in treating or preventing such disorder.

37. A method for treating or preventing gastrointestinal disorders such as emesis in a mammal, comprising administering to said mammal an amount of a compound according to claim 1, or a pharmaceutically acceptable salt thereof, that is effective in treating or preventing such disorder.

38. A method for treating or preventing chemical abuse, chemical dependencies or substance abuse in a mammal, comprising administering to said mammal an amount of a compound according to claim 1, or a pharmaceutically acceptable salt thereof, that is effective in treating or preventing such disorder.

39. A method for treating or preventing vascular and cardiovascular disorders such as congestive heart failure and hypertension in a mammal, comprising administering to said mammal an amount of a compound according to claim 1, or a pharmaceutically acceptable salt thereof, that is effective in treating or preventing such disorder.

40. A method for treating or preventing ocular disorders in a mammal, comprising administering to said mammal an amount of a compound according to claim 1, or a pharmaceutically acceptable salt thereof, that is effective in treating or preventing such disorder.

41. A method for treating or preventing sleep disorders in a mammal, comprising administering to said mammal an amount of a compound according to claim 1, or a pharmaceutically acceptable salt thereof, that is effective in treating or preventing such disorder.

42. A pharmaceutical composition for treating or preventing disorders of the dopamine system in a mammal, comprising administering to said mammal an amount of a compound according to claim 1, or a pharmaceutically acceptable salt thereof, that is effective in treating or preventing such disorder.

43. A pharmaceutical composition for treating or preventing psychotic disorders such as affective psychosis, schizophrenia, and schizoaffective disorders in a mammal, comprising administering to said mammal an amount of a compound according to claim 1, or a pharmaceutically acceptable salt thereof, that is effective in treating or preventing such disorder.

44. A pharmaceutical composition for treating or preventing movement disorders such as extrapyramidal side effects from neuroleptic agents, neuroleptic malignant syndrome, tardive dyskinesia, or Gilles De La Tourette's syndrome in a mammal, comprising administering to said mammal an amount of a compound according to claim 1, or a pharmaceutically acceptable salt thereof, that is effective in treating or preventing such disorder.

45. A pharmaceutical composition for treating or preventing movement disorders such as Parkinson's disease or Huntington's disease in a mammal, comprising administering to said mammal an amount of a compound according to claim 1, or a pharmaceutically acceptable salt thereof, that is effective in treating or preventing such disorder.

46. A pharmaceutical composition for treating or preventing gastrointestinal disorders such as gastric acid secretion in a mammal, comprising administering to said mammal an amount of a compound according to claim 1, or a pharmaceutically acceptable salt thereof, that is effective in treating or preventing such disorder.

47. A pharmaceutical composition for treating or preventing gastrointestinal disorders such as emesis in a mammal, comprising administering to said mammal an amount of a compound according to claim 1, or a pharmaceutically acceptable salt thereof, that is effective in treating or preventing such disorder.

48. A pharmaceutical composition for treating or preventing chemical abuse, chemical dependencies or substance abuse in a mammal, comprising administering to said mammal an amount of a compound according to claim 1, or a pharmaceutically acceptable salt thereof, that is effective in treating or preventing such disorder.

49. A pharmaceutical composition for treating or preventing vascular and cardiovascular disorders such as congestive heart failure and hypertension in a mammal, comprising administering to said mammal an amount of a compound according to claim 1, or a pharmaceutically acceptable salt thereof, that is effective in treating or preventing such disorder.

50. A pharmaceutical composition for treating or preventing ocular disorders in a mammal, comprising administering to said mammal an amount of a compound according to claim 1, or a pharmaceutically acceptable salt thereof, that is effective in treating or preventing such disorder.

51. A pharmaceutical composition for treating or preventing sleep disorders in a mammal, comprising administering to said mammal an amount of a compound according to claim 1, or a pharmaceutically acceptable salt thereof, that is effective treating or preventing such disorder.

52. A compound of formula IV

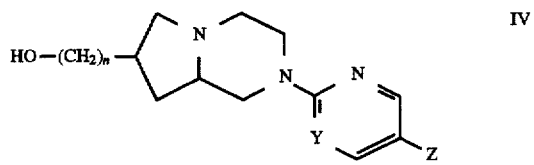

wherein n is 0 or 1;

Y is CH or N;

Z is chloro or fluoro;

all stereoisomers thereof;

which are useful intermediates for the preparation of compounds of formula I.

53. A compound of claim 52 which is (7S,8aS)-7-hydroxymethyl-2-(5-chloropyridin-2-yl)-1,2,3,4,6,7,8,8a-octahydro-pyrrolo[1,2-a]pyrazine.

54. A compound of claim 52 which is (7S,8aS)-7-hydroxymethyl-2-(5-fluoro-pyrimidin-2-yl)-1,2,3,4,6,7,8,8a-octahydro-pyrrolo[1,2-a]pyrazine.

55. A compound of claim 52 which is (7R,8aS)-7-hydroxy-2-(5-chloropyridin-2-yl)-1,2,3,4,6,7,8,8a-octahydro-pyrrolo[1,2-a]-pyrazine.

56. A compound of claim 52 which is (7R,8aS)-7-hydroxy-2-(5-fluoropyrimidin-2-yl)-1,2,3,4,6,7,8,8a-octahydro-pyrrolo[1,2-a]-pyrazine.

57. A compound of claim 52 which is (7S,8aS)-7-hydroxy-2-(5-chloropyridin-2-yl)-1,2,3,4,6,7,8,8a-octahydro-pyrrolo[1,2-a]-pyrazine.

58. A compound of claim 52 which is (7S,8aS)-7-hydroxy-2-(5-fluoropyrimidin-2-yl)-1,2,3,4,6,7,8,8a-octahydro-pyrrolo[1,2-a]-pyrazine.

* * * * *

UNITED STATES PATENT AND TRADEMARK OFFICE
CERTIFICATE OF CORRECTION

PATENT NO. : 5,714,487

DATED : February 3, 1998

INVENTOR(S) : Mark A. Sanner

It is certified that error appears in the above-identified patent and that said Letters Patent is hereby corrected as shown below:

In column 6, on lines 22-23, delete "administering to said mammal an amount of"; and on line 25, after "such disorder" add --, and a pharmaceutically acceptable carrier--;

on lines 29-30, delete "administering to said mammal an amount of"; and on line 32, after "such disorder" add --, and a pharmaceutically acceptable carrier--;

on line 38, delete "administering to said mammal an amount of"; and on line 41, after "such disorder" add --, and a pharmaceutically acceptable carrier--;

on lines 45-46, delete "administering to said mammal an amount of"; and on line 48, after "such disorder" add --, and a pharmaceutically acceptable carrier--;

on line 52, delete "administering to said mammal an amount of"; and on line 55, after "such disorder" add -- and a pharmaceutically acceptable carrier--;

on line 59, delete "administering to said mammal an amount of"; and on line 62, after "such disorder" add --, and a pharmaceutically acceptable carrier--;

on lines 66-67, delete "administering to said mammal an amount of"; and in column 7, on line 2, after "such disorder" add --, and a pharmaceutically acceptable carrier--;

in column 7, lines 6-7, delete "administering to said mammal an amount of"; and on line 9, after "such disorder" add --, and a pharmaceutically acceptable carrier--;

on lines 12-13, delete "administering to said mammal an amount of"; and on line 15, after "such disorder" add --, and a pharmaceutically acceptable carrier--;

on lines 18-19, delete "administering to said mammal an amount of"; and on line 21, after "such disorder" add --, and a pharmaceutically acceptable carrier--;

UNITED STATES PATENT AND TRADEMARK OFFICE
CERTIFICATE OF CORRECTION

PATENT NO. : 5,714,487
DATED : February 3, 1998
INVENTOR(S) : Mark A. Sanner

It is certified that error appears in the above-identified patent and that said Letters Patent is hereby corrected as shown below:

In claim 42, column 48, line 60, delete "administering to said mammal an amount of"; and on line 63, after "such disorder" add --, and a pharmaceutically acceptable carrier--.

In claim 43, column 49, line 1, delete "administering to said mammal an amount of"; and on line 4, after "such disorder" add --, and a pharmaceutically acceptable carrier--.

In claim 44, column 49, lines 9-10, delete "administering to said mammal an amount of"; and on line 12, after "such disorder" add --, and a pharmaceutically acceptable carrier--.

In claim 45, column 49, lines 15-16, delete "administering to said mammal an amount of"; and on line 18, after "such disorder" add --, and a pharmaceutically acceptable carrier--.

In claim 46, column 49, lines 21-22, delete "administering to said mammal an amount of"; and on line 24, after "such disorder" add --, and a pharmaceutically acceptable carrier--.

In claim 47, column 49, line 27, delete "administering to said mammal an amount of"; and on line 30, after "such disorder" add --, and a pharmaceutically acceptable carrier--.

In claim 48, column 49, lines 33-34, delete "administering to said mammal an amount of"; and on line 36, after "such disorder" add --, and a pharmaceutically acceptable carrier--.

In claim 49, column 49, line 40, delete "administering to said mammal an amount of"; and on line 43, after "such disorder" add --, and a pharmaceutically acceptable carrier--.

UNITED STATES PATENT AND TRADEMARK OFFICE
CERTIFICATE OF CORRECTION

PATENT NO. : 5,714,487
DATED : February 3, 1998
INVENTOR(S) : Mark A. Sanner

It is certified that error appears in the above-identified patent and that said Letters Patent is hereby corrected as shown below:

In claim 50, column 49, line 45 to column 50, line 1, delete "administering to said mammal an amount of"; and in column 50, on line 3, after "such disorder" add --, and a pharmaceutically acceptable carrier--.

In claim 51, column 50, lines 5-6, delete "administering to said mammal an amount of"; and on line 8, after "such disorder" add --, and a pharmaceutically acceptable carrier--.

Signed and Sealed this

Fourth Day of July, 2000

Attest:

Attesting Officer

Q. TODD DICKINSON
Director of Patents and Trademarks